(12) United States Patent
Yoon et al.

(10) Patent No.: US 9,133,492 B2
(45) Date of Patent: Sep. 15, 2015

(54) **KANAMYCIN COMPOUND, KANAMYCIN-PRODUCING *STREPTOMYCES* SPECIES BACTERIUM, AND METHOD OF PRODUCING KANAMYCIN**

(75) Inventors: Yeo Joon Yoon, Seoul (KR); Sung Ryeol Park, Goyang-si (KR); Je Won Park, Goyang-si (KR); Jae Kyung Sohng, Asan-si (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 0 days.

(21) Appl. No.: 13/642,842

(22) PCT Filed: Oct. 14, 2010

(86) PCT No.: PCT/KR2010/007041
§ 371 (c)(1),
(2), (4) Date: Dec. 18, 2012

(87) PCT Pub. No.: WO2011/132830
PCT Pub. Date: Oct. 27, 2011

(65) Prior Publication Data
US 2013/0096078 A1    Apr. 18, 2013

(30) Foreign Application Priority Data

Apr. 23, 2010 (KR) .................. 10-2010-0037709
Aug. 25, 2010 (KR) .................. 10-2010-0082418

(51) Int. Cl.
*C07H 15/22* (2006.01)
*C12P 19/48* (2006.01)
*A61K 31/351* (2006.01)
*A61K 31/7036* (2006.01)
*C12N 15/52* (2006.01)

(52) U.S. Cl.
CPC ............ *C12P 19/485* (2013.01); *A61K 31/351* (2013.01); *A61K 31/7036* (2013.01); *C07H 15/22* (2013.01); *C12N 15/52* (2013.01)

(58) Field of Classification Search
None
See application file for complete search history.

(56) References Cited

U.S. PATENT DOCUMENTS 5,200,327 A    4/1993    Garvin et al.

FOREIGN PATENT DOCUMENTS

| KR | 1991-0003096 A | 2/1991 |
|----|----------------|--------|
| KR | 2003-0013450 A | 2/2003 |
| WO | 2007/041156 A2 | 4/2007 |

OTHER PUBLICATIONS

Nepal et al., "Heterologous Production of Paromamine in *Streptomyces lividans* TK24 Using Kanamycin Biosynthetic Genes from *Streptomyces kanamyceticus* ATCC12853," *Mol. Cells* 27:601-608, May 31, 2009.
Park, "Characterization of the Biosynthetic Route to 4,6-disubstituted Aminoglycosides using Heterologous Expression System," Ph.D. Dissertation, Ewha University, Feb. 28, 2010.

*Primary Examiner* — Traviss C McIntosh, III
(74) *Attorney, Agent, or Firm* — Seed IP Law Group PLLC

(57) ABSTRACT

Vectors expressing kanA-kanB-kanK and other kanamycin production-related genes, *Streptomyces* species recombinant bacteria transformed with the vectors, a method of producing kanamycin antibiotics by the bacteria, and a new kanamycin compound produced by the bacterium are provided. With the use of the recombinant bacteria of the present invention, the direct fermentative biosynthesis of amikacin and tobramycin as semi-synthetic kanamycins is possible, and the yield of kanamycin B as a precursor of the semi-synthetic kanamycin is improved.

6 Claims, 4 Drawing Sheets

KANAMYCIN COMPOUND, KANAMYCIN-PRODUCING *STREPTOMYCES* SPECIES BACTERIUM, AND METHOD OF PRODUCING KANAMYCIN

CROSS-REFERENCE TO RELATED APPLICATIONS

This application is a U.S. national stage application filed under 35 U.S.C. §371 of International Patent Application PCT/KR2010/007041, accorded an international filing date of Oct. 14, 2010; which application claims priority to Korea Patent Application No. 10-2010-0037709 filed Apr. 23, 2010 and Korea Patent Application No. 10-2010-0082418 filed Aug. 25, 2010; which applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310179_405USPC_SEQUENCE_LISTING.txt. The text file is about 47 KB, created on Oct. 22, 2012, and is being submitted electronically via EFS-Web.

TECHNICAL FIELD

The present invention relates to a new kanamycin compound, a kanamycin-producing *Streptomyces* species bacterium, and a method of producing kanamycin using the bacterium.

BACKGROUND ART

Kanamycin produced by *Streptomyces kanamyceticus* is a 4,6-disubstituted 2-deoxystreptamine-containing aminoglycoside antibiotic as are gentamicins and tobramycin, whereas neomycins and butirosins are 4,5-disubstituted aminoglycosides.

These types of antibiotics are produced mainly by actinomycetes and have been widely used for a long time. Like other antibiotics, the appearance of aminoglycoside-resistant bacteria, which produce aminoglycoside-modifying enzymes, cause serious problems. The issue of resistance has been addressed by the semi-synthetic variants of naturally-occurring aminoglycosides such as amikacin, dibekacin, and arbekacin. The central 2-deoxystreptamine (2-DOS) and pseudodisaccharides 2'-N-acetylparomamine, paromamine, and neamine are common biosynthetic intermediates of most aminoglycosides. The biosynthetic route to neamine via 2-deoxystreptamine and paromamine was elucidated using recombinant enzymes involved in butiroin and neomycin biosynthesis.

DISCLOSURE OF INVENTION

Technical Problem

It has been reported a glycosyltransferase (GT) KanE (also called KanM2) from the kanamycin cluster, catalyzes the glycosylation of paromamine to produce 3"-deamino-3"-hydroxykanamycin C using uridine 5'-diphospho-D-glucose (UDP-Glc) as a cosubstrate. Alternatively, it is considered that kanamycin C and kanamycin B are produced as kanosamine (Kns: D-3-glucosamine) is transferred to paromamine and neamine, respectively, by KanE. Otherwise, it is considered that 3"-deamino-3"-hydroxykanamycin C is a precursor of kanamycin C, which can produce kanamycin B as position C-6' of kanamycin C is aminated. It is also considered that kanamycin A can be synthesized by either KanE-catalyzed addition of kanosamine to 2'-deamino-2'-hydroxyneamine or by deamination of the position C-2' of kanamycin B. However, the biosynthesis of kanamycin from pseudodisaccharides or 3"-deamino-3"-hydroxykanamycin C has not been well known. The reason for this is that it is difficult to engineer aminoglycoside-producing actinomycetes genetically and obtain functional, soluble biosynthetic enzymes.

The inventors of the present invention have constructed an effective heterologous expression system based on an engineered strain of *S. venezuelae* and elucidated the biosynthesis of gentamicin $A_2$.

Therefore, an object of the present invention is to elucidate the biosynthetic pathway of kanamycins and provide a method of producing kanamycin compounds and a new antibiotic produced by the same.

Solution to Problem

Recently, the inventors of the present invention isolated the kanamycin biosynthetic gene cluster from *S. kanamyceticus*. The production of kanamycin A by expression of this entire cluster in an aminoglycoside non-producing *S. venezuelae* indicated it contains all of the genes sufficient for the biosynthesis of the kanamycin complex.

Therefore, the object of the present invention can be achieved by a vector comprising kanA-kanB-kanK and other kanamycin biosynthetic genes, a *Streptomyces* species bacterium transformed with the vector, a method for production of kanamycin by the bacterium, and a new kanamycin compound produced by the bacterium.

Advantageous Effects of Invention

According to the present invention, a kanamycin-producing *Streptomyces* species bacterium, a method for effective production of kanamycin, and a new kanamycin compound produced by the same are provided.

BRIEF DESCRIPTION OF DRAWINGS

The above and other features and advantages of the present invention will be more clearly understood from the following detailed description taken in conjunction with the accompanying drawing, in which:

In FIG. 1A, kanamycin, tobramycin, and gentamicin are 4,6-disubstituted aminoglycosides, whereas butirosins and neomycins are 4,5-disubstituted aminoglycosides. They are all naturally-occurring products, whereas amikacin, dibekacin, and arbekacin are semi-synthetic aminoglycosides derived from kanamycins. AHBA is S-4-amino-2-hydroxybutyric acid. FIG. 1B shows the biosynthesis of compound 5 (solid lines). However, a complete biosynthetic pathway (dotted lines) for compound 8 as a final product has not been discovered. 2-DOI: 2-deoxy-scyllo-inosose; 2-DOIA: 2-deoxy-scyllo-inosamine; UDP-GlcNAc: uridine 5'-diphospho-D-2-N-acetylglucosamine; and UDP-Glc: UDP-D-glucose.

FIG. 2A shows the chromatograms of extracts from the recombinants (2-DOS, DOSf, and PAR) expressing kanA-kanB-kanK (2-DOS biosynthetic genes), kanA-kanB-kanK-kanF (kanF is a gene encoding the first glycosyltransferase), and kanA-kanB-kanK-kanF-kacA (kacA is a gene encoding deacetylase). Each colored block represents an annotated gene. FIG. 2B shows the chromatograms of compounds 2 and 9 produced by the first glycosyltransferase KanF using three kinds of UDP sugars such as UDP-glucose (Glc), UDP-2-N-acetylglucosamine (GlcNAc), and UDP-2-glucosamine (GlcN) as substrates. Each box represents the cell-free extract obtained from the recombinant host expressing kanF, and black-framed boxes indicate the boiled cell-free extracts as controls. FIG. 2C shows the chromatograms of extracts from the recombinant (PARcd) expressing kanA-kanB-kanK-kanF-kacA and kanC-kanD at the same time and the recombinant (PARil) expressing kanA-kanB-kanK-kanF-kacA and kanI-kacL at the same time. FIG. 2D shows the chromatograms of compounds 4 and 10 produced by KanI-KacL-catalyzed reaction using paromamine and 2'-deamino-2'-hydroxyparomamine as substrates. FIG. 2E shows the chromatograms of the extracts from the recombinant (KCXΔcΔd) expressing kanA-kanB-kanK-kanF-kacA-kanE, the recombinant (KCX) expressing kanA-kanB-kanK-kanF-kacA-kanE-kanC-kanD, the recombinant (KABΔcΔd) expressing kanA-kanB-kanK-kanF-kacA-kanE-kanI-kacL, and the recombinant (KAB) expressing kanA-kanB-kanK-kanF-kacA-kanE-kanC-kanD-kanI-kacL. FIG. 2F shows the chromatograms of KanC-KanD and KanE-catalyzed production of compounds 5 and 6, supplemented with paromamine and UDP-Glc. Arrows represent quenching of sequential reactions. FIG. 2G shows the chromatograms of KanC-KanD and KanE-catalyzed production of compounds 7 and 13, supplemented with paromamine and UDP-Glc. FIG. 2H shows the chromatograms of the KanI-KacL-catalyzed production of compounds 7 and 8.

FIG. 4A shows the chromatograms of extracts from the recombinants expressing kanA-kanB-kanK and kanF (DOSf), nemD (DOSn), tobM1 (DOSt$_1$) or gtmG (DOSg) at the same time, in which the bar graph on the right side shows the yield of kanamycin pseudodisaccharide intermediates produced by each recombinant strain. The white bar indicates compound 2 and the gray bar indicates compound 9. Data were obtained from triplicate analyses. FIG. 4B shows the chromatograms of extracts from recombinants (KCX, KCXΔfn, KCXΔft$_1$, and KCXΔfg) expressing one of kanA-kanB-kanK-kacA-kanE-kanC-kanD, together with kanF, nemD, tobM1, or gtmG. The bar graph shows the yield of kanamycin pseudodisaccharides produced by each recombinant strain. The white bar indicates compounds 5 and 6, which are the congeners of compound 7 in the left-hand cycle of the decalcomania-like biosynthetic pathway. The gray bars indicate yields of compounds 11 and 12, which are the congeners of compound 8 in the right-hand cycle. FIG. 4C shows the chromatograms of extracts from recombinants (KAB and KABΔfn) expressing one of kanA-kanB-kanK-kacA-kanE-kanC-kanD-kanI-kacL together with kanE or nemD, in which the bar graph shows the yield of kanamycin produced by each recombinant. The white bars indicate the production of compounds 6 and 7, and the gray bar represents the production of compounds 12 and 8.

FIG. 5A shows the chromatograms of the products from the recombinant (KCXb) expressing a compound 12-producing gene set (kanA-kanB-kanK-kacA-kanE-kanC-kanD) together with seven butirosin biosynthetic genes (btrG-btrH-btrI-btrJ-btrK-btrO-btrV) or the recombinant (KABb) expressing a compound 8-producing gene set (kanA-kanB-kanK-kacA-kanE-kanC-kanD-kanI-kacL). Compound 15 is the AHBA-conjugated kanamycin derivative amikacin and compound 17 is the previously uncharacterized AHBA-conjugated kanamycin derivative 1-N-AHBA-kanamycin X. FIG. 5B shows the chromatograms of the products from the recombinants (KABΔfna and KABΔfnΔet$_2$a) expressing aprD3-aprD4 and a compound 8-biosynthetic gene set such as kanA-kanB-kanK-nemD-kacA-kanE-kanC-kanD-kanI-kacL or kanA-kanB-kanK-nemD-kacA-tobM2-kanC-kanD-kanI-kacL at the same time. Compounds 16 and 18 are tobramycin and nebramine as a tobramycin biosynthetic intermediate. FIG. 5C shows the structures of kanamycin analogs produced by the recombinants expressing aprD3-aprD4 and tobM2 genes. Each colored-circle represents the functional group formed by the product of the gene with annotation information shown by the same colored block.

FIG. 6A shows the chromatograms of the production of compounds 11 and 12. Each box represents the cell-free extract obtained from the recombinant host expressing kanE or kanC-kanD, black-framed boxes indicate the boiled cell-free extracts as controls, and arrows represent quenching of sequential reactions. FIG. 6B shows the chromatograms of the production of compounds 8 and 14.

BEST MODE FOR CARRYING OUT THE INVENTION

Figure 1:
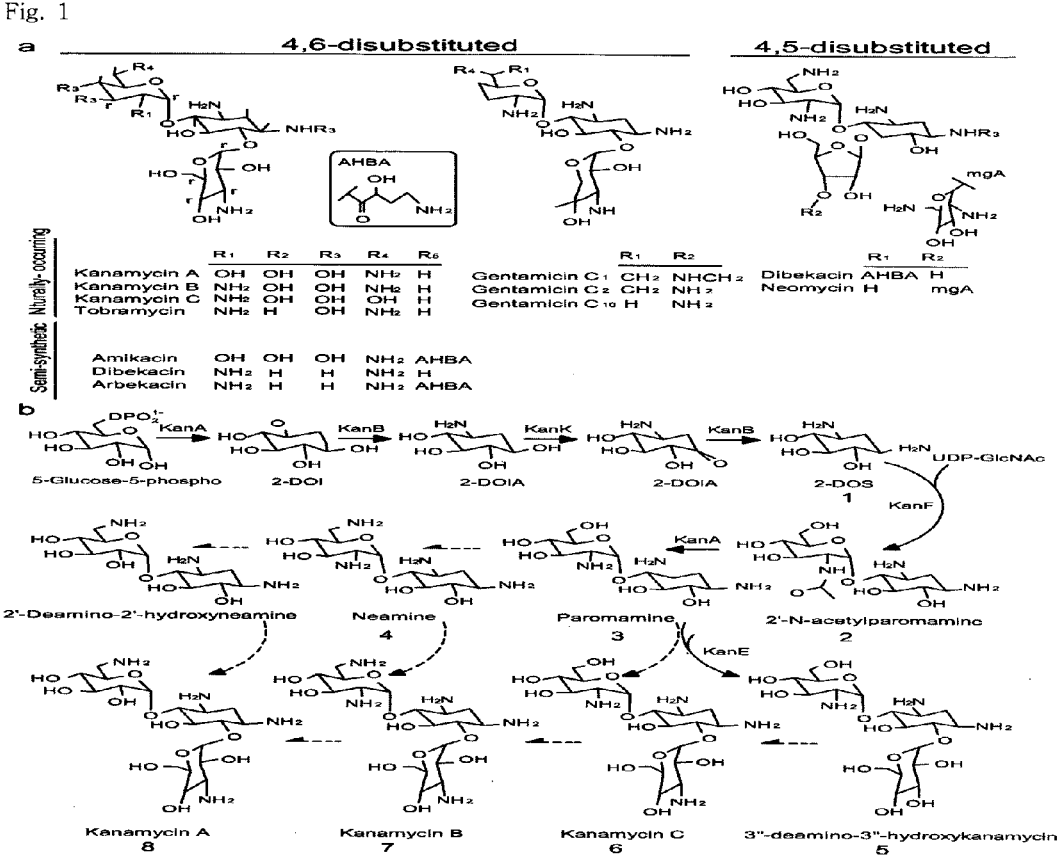
FIG. 1A shows the structures of 2-DOS-containing aminoglycosides and FIG. 1B shows the previously proposed biosynthetic pathway of kanamycins.

The present invention provides a vector comprising at least one gene set selected from the group consisting of:
(1) kanA, kanB, and kanK (DOS strain);
(2) kanA, kanB, kanK, and kanF (DOSf strain);
(3) kanA, kanB, kanK, kanF, and kacA (PAR strain);
(4) kanA, kanB, kanK, kanF, kacA, kanC, and kanD (PARcd strain);
(5) kanA, kanB, kanK, kanF, kacA, kanI, and kacL (PARil strain);
(6) kanA, kanB, kanK, kanF, kacA, and kanE (KCXΔcΔd strain);
(7) kanA, kanB, kanK, kanF, kacA, kanE, kanC, and kanD (KCX strain);
(8) kanA, kanB, kanK, kanF, kacA, kanE, kanI, and kacL (KABΔcΔd strain);
(9) kanA, kanB, kanK, kanF, kacA, kanE, kanC, kanD, kanI, and kacL (KAB strain);
(10) kanA, kanB, kanK, kanF, kacA, kanE, kanC, kanD, btrG, btrH, btrI, btrJ, btrK, btrO, and btrV (KCXb strain);
(11) kanA, kanB, kanK, kanF, kacA, kanE, kanC, kanD, kanI, kacL, btrG, btrH, btrI, btrJ, btrK, btrO, and btrV (KABb strain);
(12) kanA, kanB, kanK, and nemD (DOSn strain);
(13) kanA, kanB, kanK, nemD, kacA, kanE, kanC, and kanD (KCXΔfn strain);
(14) kanA, kanB, kanK, nemD, kacA, kanE, kanC, kanD, kanI, and kacL (KABΔfn strain);
(15) kanA, kanB, kanK, nemD, kacA, kanE, kanC, kanD, kanI, kacL, aprD3, and aprD4 (KABΔfna strain);
(16) kanA, kanB, kanK, nemD, kacA, tobM2, kanC, kanD, kanI, kacL, aprD3, and aprD4 (KABΔfnΔet$_2$a strain);
(17) kanA, kanB, kanK, and tobM1 (DOSt$_1$ strain);
(18) kanA, kanB, kanK, tobM1, kacA, kanE, kanC, and kanD (KCXΔft$_1$ strain);
(19) kanA, kanB, kanK, and gtmG (DOSg strain); and
(20) kanA, kanB, kanK, gtmG, kacA, kanE, kanC, and kanD (KCXΔfg strain), and
a kanamycin-producing recombinant *Streptomyces* species bacterium transformed with the vector.

Preferably, the kanA, kanB, kanK, kanF, kacA, kanE, kanC, kanD, kanI, and kacL are derived from *Streptomyces kanamyceticus* and have sequence numbers 5 to 14.

The aprD3, aprD4, tobM1, and tobM2 are derived from *Streptomyces tenebrarius* and have sequence numbers 15 to 18.

The btrG, btrH, btrI, btrJ, btrK, btrO, and btrV are derived from *Bacillus circulans* and have sequence numbers 19 to 25.

The nemD is derived from *Streptomyces fradiae* and has sequence number 26.

The gtmG is derived from *Micromonospora echinospora* and has sequence number 4.

Preferably, the *Streptomyces* species bacterium further expresses a kanamycin-resistant gene. Preferably, the kanamycin-resistant gene comprises gtmF, gtmK, and gtmL derived from *Micromonospora echinospora*, which have sequence numbers 1 to 3.

The *Streptomyces* species bacterium is *Streptomyces venezuelae*, but not limited thereto. Preferably, the *Streptomyces* species bacterium is *Streptomyces venezuelae* KCTC11725BP and, more preferably, the *Streptomyces* species bacterium is *Streptomyces venezuelae* KCTC11726BP. The *Streptomyces* species bacterium is *Streptomyces venezuelae* KCTC11727BP and, preferably, the *Streptomyces* species bacterium is *Streptomyces venezuelae* KCTC11728BP.

Moreover, the present invention provides a method of producing a kanamycin antibiotic using the *Streptomyces* species bacterium, and the kanamycin antibiotic produced by the present invention comprises the following compounds 1 to 20:
Compound 1: 2-deoxystreptamine (2-DOS)
Compound 2: 2'-N-acetylparomamine;
Compound 3: paromamine;
Compound 4: neamine;
Compound 5: 3"-deamino-3"-hydroxykanamycin C;
Compound 6: kanamycin C;
Compound 7: kanamycin B;
Compound 8: kanamycin A;
Compound 9: 2'-deamino-2'-hydroxyparomamine;
Compound 10: 2'-deamino-2'-hydroxyneamine
Compound 11: 3"-deamino-3"-hydroxykanamycin X;
Compound 12: kanamycin X;
Compound 13: 3"-deamino-3"-hydroxykanamycin B;
Compound 14: kanamycin D;
Compound 15: amikacin;
Compound 16: tobramycin;
Compound 17: 1-N-AHBA-kanamycin X;
Compound 18: nebramine;
Compound 19: 3'-deoxykanamycin C; and
Compound 20: 3'-deoxykanamycin A.

Moreover, the products obtained from the recombinant bacteria are as follows:
DOS: compound 1;
DOSf: compounds 2 and 9;
PAR: compounds 3 and 9;
PARcd: compounds 3 and 9;
PARil: compounds 4 and 10;
KCXΔcΔd: compounds 5 and 11;
KCX: compounds 6 and 12;
KABΔcΔd: compounds 13 and 14;
KAB: compounds 7 and 8;
KCXb: compound 17;
KABb: compound 15;
DOSn: compounds 2 and 9;
KCXΔfn: compounds 6 and 12;
KABΔfn: compounds 7 and 8;
KABΔfna: compounds 18, 19 and 20;
KABΔfnΔet$_2$a: compound 16;
DOSt$_1$: compounds 2 and 9;
KCXΔft$_1$: compounds 6 and 12;
DOSg: compounds 2 and 9; and
KCXΔfg: compounds 6 and 12.

When the kanamycin is produced by the gene recombinant bacteria of the present invention, especially KABΔfn strain, the yield of kanamycin B as a precursor of arbekacin, which is one of the semi-synthetic aminoglycosides, is improved compared to wild-type strains.

Moreover, with the use of the gene recombinant bacteria of the present invention, especially KABb and KABΔfnΔet$_2$a strains, it is possible to produce amikacin and tobramycin by direct fermentation, not by semi-fermentation and semi-synthesis.

Furthermore, the present invention provides a new compound represented by the following formula 1:

[Formula 1]

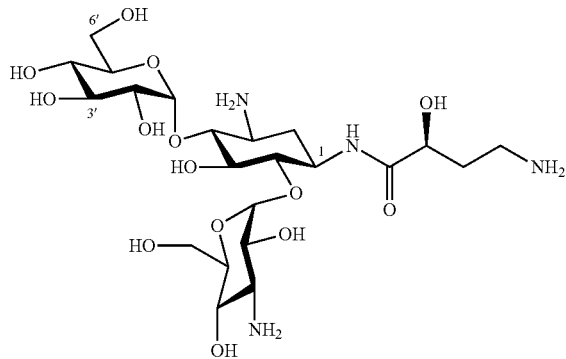

The new compound is compound 17, 1-N-AHBA-kanamycin X.

The kanamycin compound of the present invention produced by the bacterium of the present invention has an antibacterial effect. More particularly, the compound of the present invention has an antibacterial effect on Gram-negative bacteria. The compound has an antibacterial effect on *Pseudomonas aeruginosa* and *Escherichia coli*, but not limited thereto. Especially, the new compound, 1-N-AHBA-kanamycin X, has an antibacterial effect on amikacin-resistant *P. aeruginosa*.

Recently, various studies have reported that aminoglycoside antibiotics containing the 2-DOS have antiviral effects on various viruses such as bovine viral diarrhea virus (BVDV), dengue virus (DENY), etc. Moreover, many studies have reported that the aminoglycoside antibiotics, which induce mammalian ribosomes to read-through premature stop codon mutations, can treat and improve hereditary diseases such as cystic fibrosis, muscular atrophy, Hurler syndrome, telangiectasis, and Usher syndrome. The kanamycin compound of the present invention also contains the 2-DOS as a fundamental structure, and thus it is considered that the kanamycin compound of the present invention has an antiviral effect and can treat and improve such hereditary diseases.

Therefore, the present invention provides an antibacterial composition comprising the kanamycin compound as an effective ingredient.

Moreover, the present invention provides an antiviral composition comprising the kanamycin compound as an effective ingredient.

Furthermore, the present invention provides a pharmaceutical composition comprising the kanamycin compound as an effective ingredient for the treatment of at least one disease selected from the group consisting of cystic fibrosis, muscular atrophy, Hurler syndrome, telangiectasis, and Usher syndrome.

The composition may be administered orally, rectally, vaginally, topically, transdermally, intravenously, intramuscularly, intraperitoneally, or subcutaneously. The effective dose of the active compound may vary depending on the minimum inhibitory concentration (MIC), the age and condition of the patient, particular disease, the severity of disease or condition, the route of administration, and administrator s decision.

The pharmaceutical composition may be medicated in the form of solid, semi-solid, or liquid depending on an administration pattern. It may include tablets, powders, suppositories, granules, creams, lotions, ointments, patches, aqueous solutions, suspensions, dispersions, emulsions, syrups, but are not limited to them. Active ingredients can be encapsulated in liposomes, nanoparticles, microcapsules, etc. Solid compositions such as tablets, pills, granules, etc. may be coated for convenience.

The composition of the present invention may contain pharmaceutically acceptable excipients such as diluents, carriers, isotoners, stabilizers, antioxidants, binders, colorants, flavorings, preservatives, thickening agents, etc. Such excipients can be selected by one skilled in the art according to the administration routes and formulations. Moreover, the composition of the present invention may contain a small amount of a non-toxic adjuvant such as a wetting agent, emulsifier, pH buffer agent, etc. The non-toxic adjuvant may include, but not limited to, acetate, sorbitan monolaurate, triethanolamine, and triethanolamine oleate. The composition for intravenous administration may be a solution in sterile isotonic aqueous buffer solution and may contain a local anesthetic for relief of pain in the injection area.

TABLE 1

Deoxyoligonucleotide primers used for PCR amplification of genes

| Gene | Primer sequence(5' to 3', restriction site shown with underline) | Portion of gene | Enzyme site |
|---|---|---|---|
| kanA-kanB | cccggatccgaatcccccttcgtgacg | 5' | BamHI |
|  | gtgactagtgttcgtcgaccaccgcgtcga | 3' | SpeI |
| kanK | gcttctagaactccggagcaccgtgca | 5' | XbaI |
|  | gtgaagcttcgtggtgccggacaggccta | 3' | HindIII |
| kanC | gggacctctagaacgcggtggtcgacgaac | 5' | XbaI |
|  | tcttccaagcttactagttgtcggcggtcgccccga | 3' | SpeI/HindIII |
| kanD | gaccgctctagacacctccgaggtcctctc | 5' | XbaI |
|  | tgaaaagcttactagtgggtgacgagacgccggg | 3' | SpeI/HindIII |
| kanE | acatctagaggctccggaagaccgccgacgcca | 5' | XbaI |
|  | tcgaagcttactagtgagacgaggaggaccctt | 3' | SpeI/HindIII |
| kanF | cgaggctctagagccggaccagaacccatt | 5' | XbaI |
|  | tagaacaagcttactagtacgtcgggtgtcgtacgg | 3' | SpeI/HindIII |

TABLE 1-continued

Deoxyoligonucleotide primers used for PCR amplification of genes

| Gene | Primer sequence (5' to 3', restriction site shown with underline) | Portion of gene | Enzyme site |
|---|---|---|---|
| kanI-kacL | gatcgctctagacacctggttctggttccc | 5' | XbaI |
|  | aggggaaagcttactagtgtcaggagatgccgaccg | 3' | SpeI/HindIII |
| kacA | ggcgtctagataccgggagatcgggctgtg | 5' | XbaI |
|  | acaaagcttactagttgctcatagcgactccttgt | 3' | SpeI/HindIII |
| nemD | cactctagacatcgccgtcctctcccgt | 5' | XbaI |
|  | tcaaagcttactagtggcgcagatacggcgcac | 3' | SpeI/HindIII |
| tobM1 | ccgtctagaccgcccttcccccgcaac | 5' | XbaI |
|  | gataagcttactagtcacaccgtcctattcctg | 3' | SpeI/HindIII |
| tobM2 | cgatctagaccgggaggcgaccgtgt | 5' | XbaI |
|  | gcgaagcttactagttcagacgcatacgcccag | 3' | SpeI/HindIII |
| gtmG | tgtcctctagagctgcccggtcacttcccgc | 5' | XbaI |
|  | aaaaagcttactagtcactcttccggaagaatc | 3' | SpeI/HindIII |
| btrG-btrH | ttctctagatctaggaaaccgcatgcc | 5' | XbaI |
|  | ggctacgtaaaactagtggtttatccgcttttgct | 3' | SpeI/SnaBI |
| btrI-btrJ | acctctagacggaaaccgccatcccat | 5' | XbaI |
|  | tcctacgtaaaactagtgagttaatgaacagccgt | 3' | SpeI/SnaBI |
| btrK-btrO | agctctagaaagcccgaagcctgcttg | 5' | XbaI |
|  | gtttacgtaaaactagttccctagaccggattcga | 3' | SpeI/SnaBI |
| btrV | tattctagaattgacttataactcaat | 5' | XbaI |
|  | cattacgtaaaactagtatccgaacgtcacataag | 3' | SpeI/SnaBI |
| aprD3 | ggttctagatgatggacgtggccgcga | 5' | XbaI |
|  | cttaagcttactagtgggccgtcggtcgtcctg | 3' | SpeI/HindIII |
| aprD4 | ggctctagaaacccaccctcaccatccag | 5' | XbaI |
|  | cgcaagcttactagtatcgtgtggtctccggct | 3' | SpeI/HindIII |

The inventors of the present invention have reconstructed a complete biosynthesis of kanamycin by integrating the plasmid containing various candidate genes isolated from *S. kanamyceticus* into *S. venezuelae* strain, which is deficient in biosynthesis of the endogenous deoxysugar thymidine 5'-diphospho (TDP)-D-desosamine. The inventors have amplified putative kanamycin biosynthetic genes by PCR with specific primers shown in table 1.

The inventors have modified the kanamycin biosynthetic flux to produce kanamycin B (compound 7) as a main product. The reason for this is that the production of compound 7 leads to the production of 3'-deoxykanamycin and 1-N-AHBA kanamycin by direct fermentation, which will be valuable substitutes for the chemical synthesis of dibekacin and arbekacin.

After examining the kanamycin analogs obtained from the recombinants and their structures, it has been confirmed that the kanamycin antibiotic, which is known as one of the compounds produced from the recombinant bacteria of the present invention, has the same properties as the commercially available standard kanamycin analog or the kanamycin analog derived from *S. kanamyceticus*. However, it has been ascertained that 1-N-AHBA-kanamycin X, a new kanamycin analog, has been produced by the recombinant heterologous strain of the present invention in addition to the conventional kanamycin antibiotics.

First, compound 3 was biosynthesized from Glc-6-phosphate as shown in FIG. 1B. As expected, the recombinant heterologous strain expressing kanA-kanB-kanK (DOS strain) produced compound 1 (21.4 μM) (FIG. 2A). To confer resistance to kanamycin in *S. venezuelae* without modifying the aminoglycoside structure, three resistance genes gtmF-gtmK-gtmL from the gentamicin gene cluster were introduced into the recombinant heterologous strain. Transformants expressing these genes were resistant to >10.0 mg/ml of the commercially available kanamycin compared to 1.0 μg/ml in control strains. These resistance genes were expressed together with the kanamycin biosynthetic genes in the heterologous host in subsequent experiments.

Compound 2 (1.3 μM) was produced by expressing DOS biosynthetic genes plus kanF encoding the first glycosyltransferase. Interestingly, a greater amount of compound 9 (7.1 μM) was produced at the same time. Moreover, The cell-free extract of *S. venezuelae* expressing kanF supplemented with compound 1 as a glycosyl acceptor and UDP-Glc or UDP-GlcNAc as a glycosyl donor produced 9-fold greater amount of compound 9 than that of compound 2 (FIG. 2B). Therefore, it indicates that KanF accepts both UDP-Glc and UDP-GlcNAc as cosubstrates but preferentially transfers UDP-Glc to compound 1. Compound 3 (2.2 μM) was produced by the recombinant strain (PAR strain) expressing kacA as 2'-N-acetylparomamine deacetylase together with compound 2/9 biosynthetic genes (FIG. 2A).

It is necessary to convert compound 3 into compound 4 for the kanamycin biosynthesis. It was estimated that KanI and KacL would participate in the conversion of compound 3 into compound 4 based on the in silico analysis of the aminoglycoside gene cluster. Meanwhile, it is considered that KanC and KanD are responsible for the formation of UDP-kns by aminating the C-3 hydroxyl group of UDP-Glc. Otherwise it is considered that KanC and KanD participate in the production of compound 6 from compound 5.

In one example of the present invention, kanC-kanD genes were first expressed in PAR strain (PARcd strain) to identify the functions of KanI-KacL and KanC-KanD. However, expression of kanC-kanD in the strain PAR (strain PARcd) produced only 3 and 9 (FIG. 2C), indicating that KanC-KanD does not participate in amination of the pseudodisaccharides. On the contrary, the recombinant strain (PARil strain) expressing kanI-kacL produced compound 10 (4.3 µM) as well as compound 4 (2.2 µM) (FIG. 2C). Incubation of the cell-free extracts of the recombinant expressing kanI-kacL with compounds 3 and 9 resulted in the production of compounds 4 and 10 (FIG. 2D).

In one example of the present invention, pseudotrisaccharide kanamycins were biosynthesized. Compound 5 (3.2 µM) and compound 11 (4.5 µM), which was not known as a biosynthetic intermediate, were produced by the recombinant (KCXΔcΔd strain) expressing kanE encoding a second glycosyltransferase together with genes for biosynthesis of compound 3/9 (FIG. 2E). Additional expression of kanC-kanD in KCXΔcΔd strain (KCX strain) resulted in the production of compound 6 (1.6 µM) and compound 12 (6.0 M), C-3" amination. The strain (KABΔcΔd strain) obtained by expressing kanI-kacL in KABΔcΔd strain produced compound 13 (2.0 µM) and compound 14 (3.2 µM). Moreover, the strain (KAB strain) obtained by expressing kanC-kanD in KABΔcΔd strain produced compound 7 of 1.0 mg/l (2.1 µM) and compound 8 of 3.1 mg/l (6.3 µM) (FIG. 2E).

Figure 6:
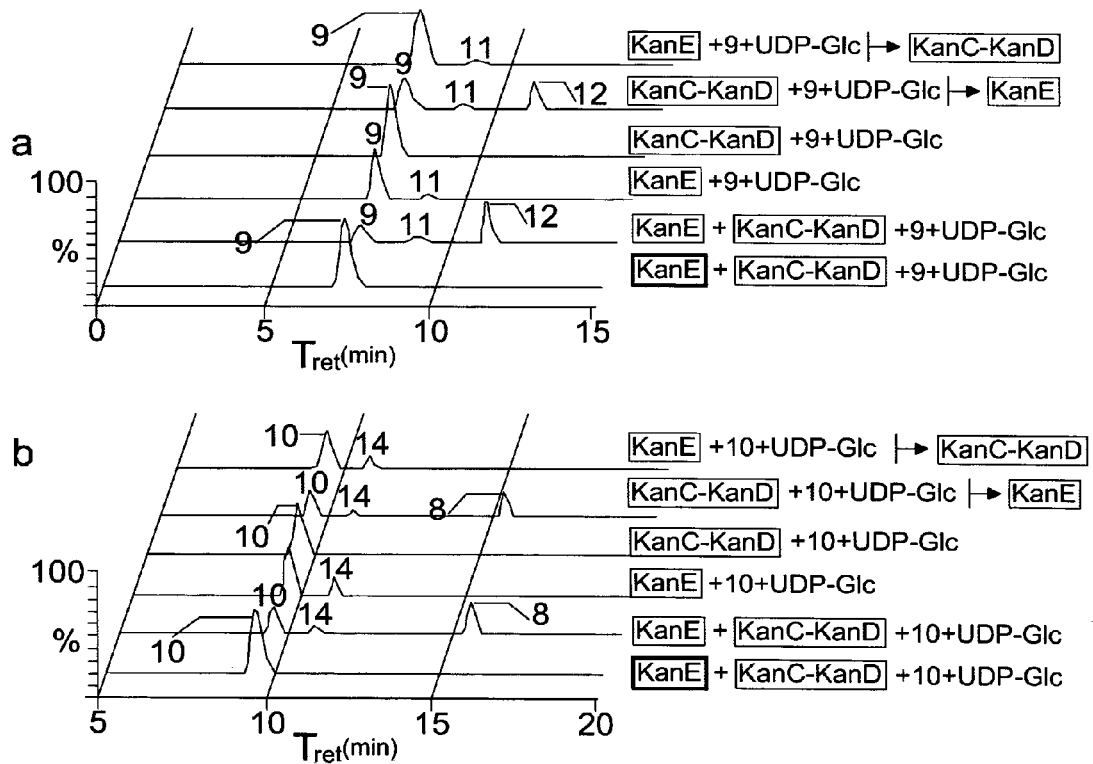
FIGS. 6A and 6B show the results of HPLC-ESI-MS/MS analysis of kanamycin pseudodisaccharides obtained from in vitro reactions using cell-free extracts of recombinant *S. venezuelae* strains expressing kanE and kanC-kanD, respectively.

In one example of the present invention, cell-free extracts of recombinant *S. venezuelae* strains expressing kanE or kanC-kanD were prepared to determine whether UDP-kns biosynthesized from UDP-Glc is linked at the C-6 position of pseudodisaccharide or whether a Glc moiety of pseudodisaccharide is converted into kanosamine. Compounds 3 and 4 were incubated with UDP-Glc to produce compounds 5/6 and 13/7, respectively. When compounds 3 and 4 and UDP-Glc were added to the cell-free extracts of the recombinant strain expressing kanE, compounds 5 and 13 were produced, respectively. When these reactions were quenched and the resulting mixture was incubated together with the cell-free extracts of the strain expressing kanC-kanD, compounds 5 and 13 remained and further conversion was not observed. However, when compounds 3 and 4 were reacted with UDP-Glc and the cell-free extracts of the strain expressing kanC-kanD, compounds 6 and 7 were produced, respectively (FIGS. 2F and 2G). The same results were observed when compounds 9 and 10 were used as substrates (FIG. 6). These results showed that the hydroxyl group of UDP-Glc was aminated before the glycosyl transfer reaction by the enzyme pair during the biosynthesis of kanosamine. This example can be observed in the biosynthesis of kanosamine in *Amycolatopsis mediterranei*, a rifamycin-producing strain.

Figure 2:
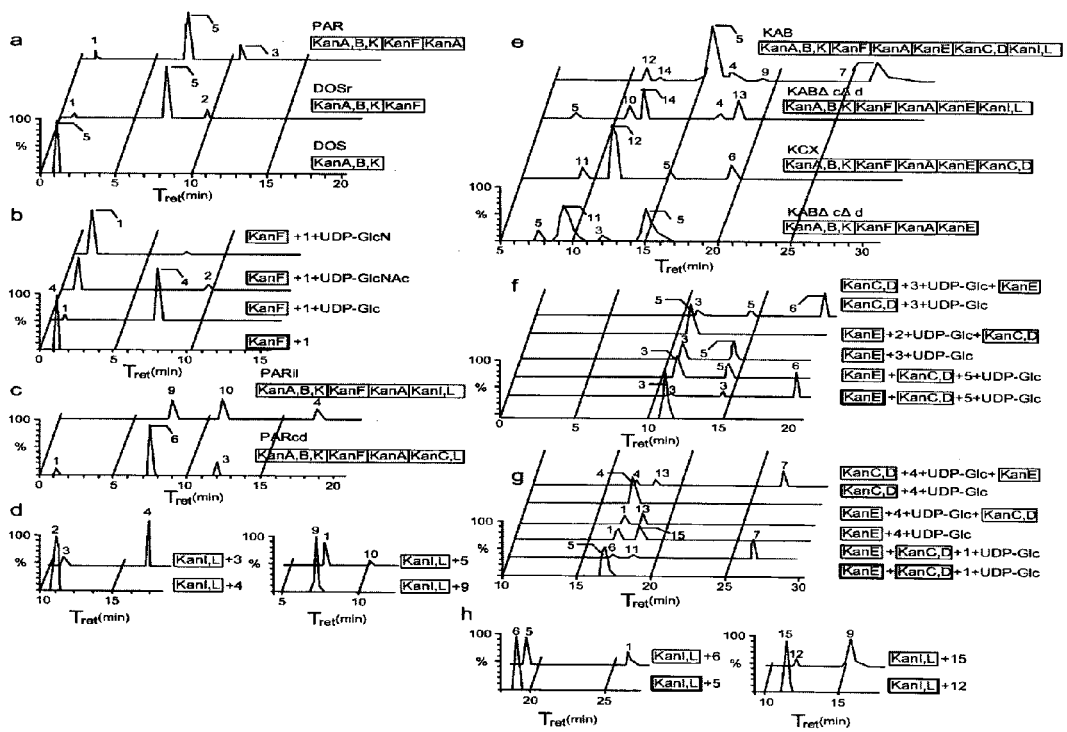
FIGS. 2A to 2H show the results of HPLC-ESI-MS analysis of kanamycin biosynthetic intermediates obtained in vitro expression of putative kanamycin gene sets in recombinant *S. venezuelae* hosts and in vitro reactions using cell-free extracts of recombinants.
Figure 3:
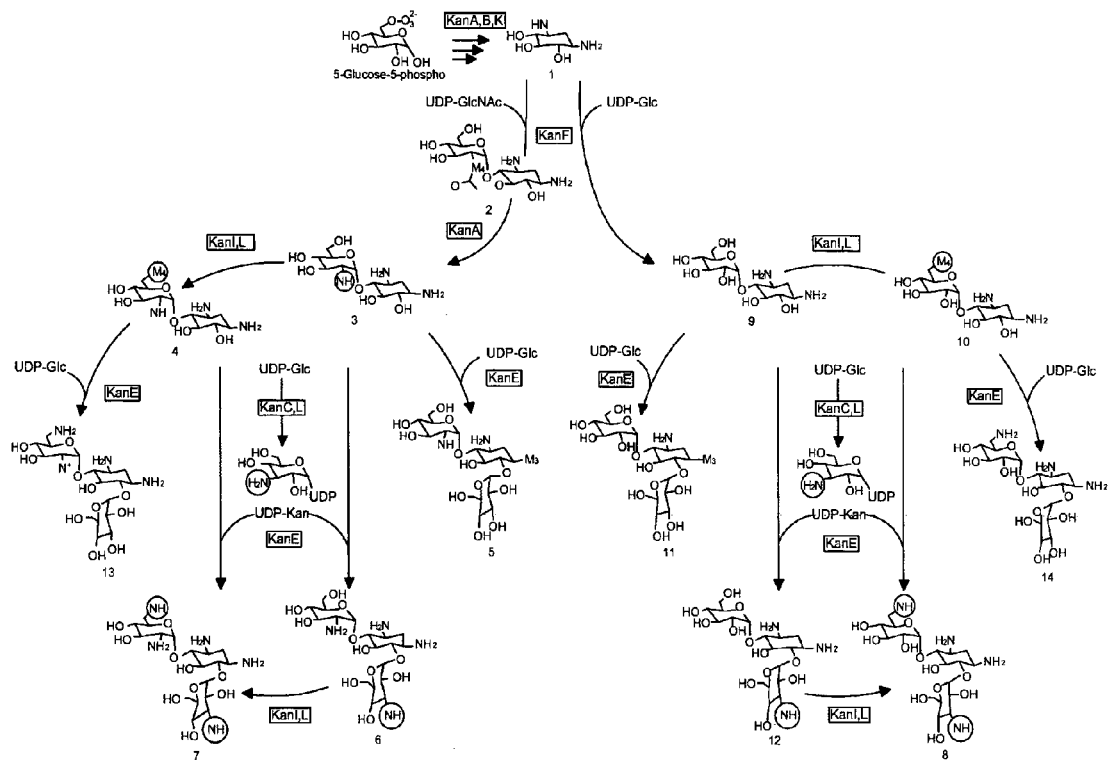
FIG. 3 shows a decalcomania-like kanamycin biosynthetic pathway, in which each colored block represents an annotated gene and its product has been proven to catalyze the biosynthesis of kanamycin intermediates. Each colored-circle represents the functional group formed by the product of the gene shown by the same colored block.

Moreover, when the cell-free extracts of the strain expressing kanI-kacL were incubated together with compounds 6 and 12, compounds 7 and 8 were produced, respectively. It is considered that KanI and KacL participate in the biosynthesis of compounds 4 and 10 as well as compounds 7 and 8 (FIGS. 2D and 2H), which shows their substrate flexibility toward pseudodi- and tri-saccharides. In summary, a decalcomania-like kanamycin biosynthetic pathway of the kanamycin complex dominated by KanF and KanE glycosyltransferases was identified (FIG. 3).

Figure 4:
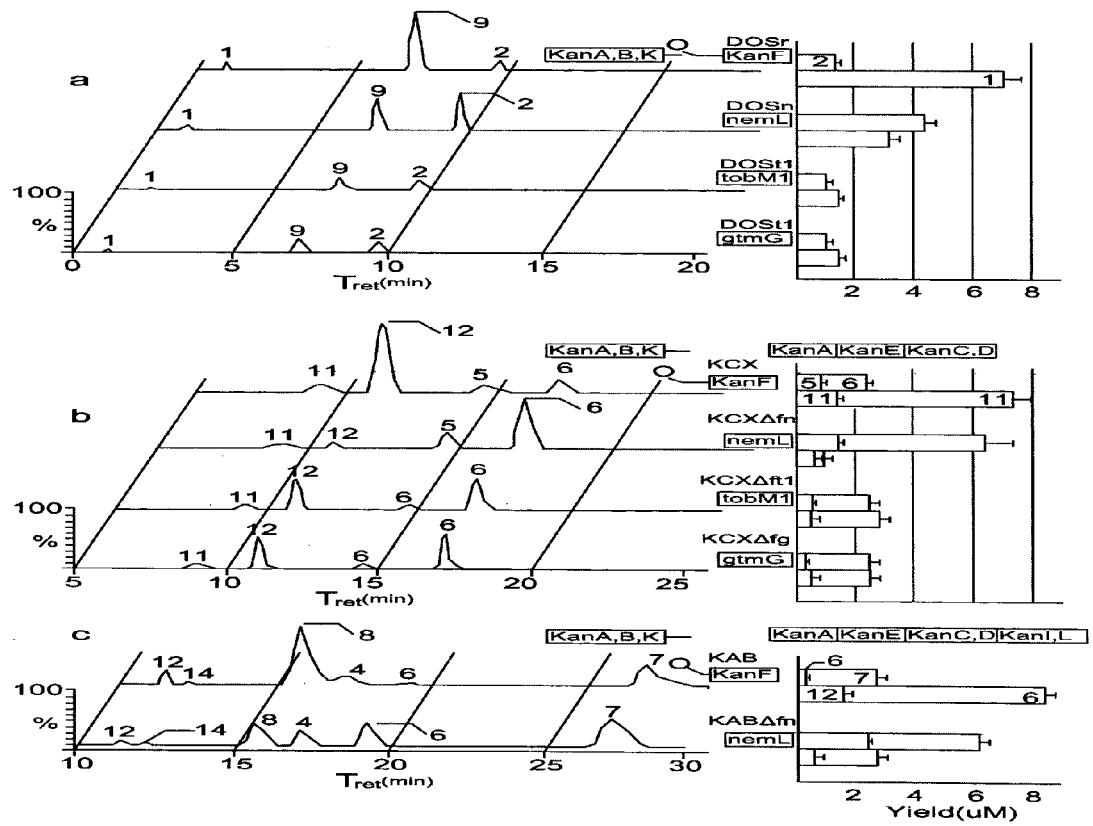
FIGS. 4A to 4C show the results of HPLC-ESI-MS/MS analysis of kanamycin biosynthetic intermediates obtained from the recombinant strains in which the first glycosyltransferase-encoding gene has been changed.

In one example of the present invention, the biosynthesis of kanamycin was modified. Compound 8 is the major fermentation product in both wild-type kanamycin producer *S. kanamyceticus* and the heterologous host *S. venezuelae*. It was shown that KanF glycosyltransferase preferred UDP-Glc to UDP-GlcNAc in the previous experiment. KanI-KacL, which preferred compound 12 to compound 6, was involved in the yield of compounds 8 and 7 (FIG. 2H). While amikacin (compound 15) can be synthesized from compound 8, the arbekacin, a latest semi-synthetic aminoglycoside having antibacterial activity against resistant bacteria, can be produced by removing the 3',4'-hydroxyl group followed by 1-N-acylation with AHBA. It was supposed that the biosynthesis of kanamycin tends to increase the yield of compound 7, if the kanF gene encoding the first glycosyltransferase was substituted with another gene encoding the glycosyltransferase which prefers UDP-GlcNAc to UDP-Glc as a glycosyl donor in the genetic construct for the biosynthesis of compounds 7 and 8. First, the inventors replaced kanF in the DOS strain with nemD, tobM1, and gtmG encoding three different glycosyltransferases from neomycin, tobramycin, and gentamicin. The DOSf strain as a control expressing kanF produced compound 2 (1.4 µM; 14% of the total pseudodisaccharide) and compound 9 (7.1 µM; 79%). On the contrary, the strain (DOSn strain) expressing nemD produced compound 2 (4.4 µM; 57%) and compound 9 (3.4 µM; 36%), from which it seemed that NemD use UDP-GlcNAc preferentially in contrast to KanF. When tobM1 and gtmG replaced kanF (DOSt$_1$ and DOSg strains), there was no significant change in the ratio of compounds 2 and 9 produced (FIG. 4A).

Moreover, in another example of the present invention, nemD, tobM1, and gtmG were separately substituted for kanF in KCX strain. When comparing the ratio of compounds 6 and 12 (1.6 µM, 16% and 6.0 µM, 60%) produced by KCX strain, the ratio of pseudodisaccharides 6 and 12 (5.0 µM, 65% and 0.4 µM, 7%) produced by the recombinant strain (KCXΔfn) expressing nemD was inverted. However, the ratio of pseudodisaccharide products 6 and 12 in the recombinant strain expressing either tobM1 (KCXΔft$_1$) or gtmG (KCXΔfg) were similar to each other (FIG. 4B). Moreover, while the yields of compounds 7 and 8 produced by KAB strain were 21% (2.3 µM) and 61% (6.8 µM), the yield of compound 7 in the strain (KABΔfn) obtained by substituting kanF with nemD was increased to 46% (FIG. 4C).

Figure 5:
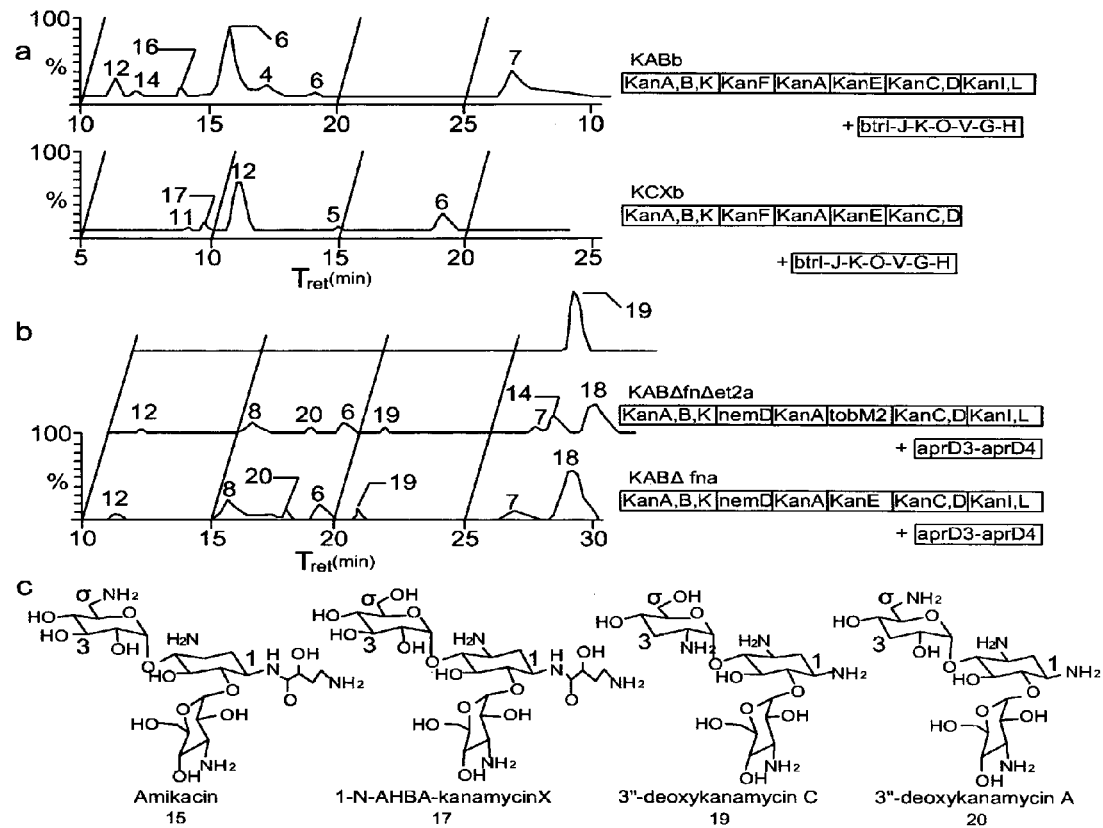
FIGS. 5A to 5C show the results of HPLC-ESI-MS/MS analysis of compounds 17, 19, and 20 produced by the recombinant strains.

In another example of the present invention, 1-N-AHBA-kanamycin and 3'-deoxykanamycin were produced by direct fermentation. The inventors have modified the kanamycin biosynthetic pathway for in vivo production of 1-N-acylated kanamycin containing AHBA such as compound 15 and 3'-deoxykanamycin such as compound 16. The AHBA molecular structure was observed in the naturally-occurring butirosin. Recently, it has been reported that the btrG-btrH-btrI-btrJ-btrK-btrO-btrV gene set is responsible for biosynthesis and introduction of the AHBA side chain into the amino group at C-1 of 2-DOS in butirosin. Compound 17 (0.6 mg/l, 1.0 µM), a new aminoglycoside compound, was produced by introducing these genes into the KCX strain. Moreover, 0.5 mg/l (0.8 µM) of compound 15 was successfully produced by expressing the btr gene set in the KAB strain (FIGS. 5A and 5C).

Moreover, the inventors have analyzed the aminoglycoside gene cluster by bioinformatics analysis to find aprD3-aprD4, two putative apramycin genes, from *S. tenebrarius*, a tobramycin (compound 16)-producing strain. It seems that the aprD3-aprD4 genes are responsible for C-3' deoxygenation of pseudodi- and/or tri-saccharides.

In one example of the present invention, the aprD3-aprD4 genes were introduced into KABΔfn engineered for the increased production of compound 7. The resulting strain KABΔfna produced compound 18 as a major product and produced compounds 19 and 20 but did not produce compound 16 (FIGS. 5B and 5C). This result shows that the activity of AprD3-AprD4 pair removes the 3'-hydroxyl group in compounds 3, 10, and 4. It also indicates the second glycosyltransferase KanE selectively transfers kanosamine to compounds 3 and 10 but not to compound 18. To select the glycosyltransferase that transfers kanosamine to compound 18 to produce compound 16, cell-free extracts of *S. kanamyceticus* and *S. tenebrarius* were prepared and incubated together with compound 18. The cell-free extract of *S. tene-*

In the test with the clinically isolated amikacin-sensitive *P. aeruginosa* strain, most kanamycin intermediates showed very low antibacterial with exception of the compounds 6, 7, 8, and 12. Interestingly, new compound 17 showed improved antibacterial activity against all the test strains compared with amikacin (compound 15). Especially, compound 15 showed no activity on the clinically isolated amikacin-resistant *P. aeruginosa* strain, whereas, compound 17 showed very strong activity (MIC ~64).

TABLE 2

Antibacterial spectra against Gram-negative bacteria

| | | MIC (µg/ml) | | | | | |
|---|---|---|---|---|---|---|---|
| | | Typical strains | | Clinically isolated strains | | | |
| Kanamycin-related aminoglycosides | | *E. coli* ATCC 25922(Kan$^S$) | *P. aeruginosa* ATCC 27853(Kan$^R$) | *E. coli* CCARM 1A020(Kan$^S$) | *E. coli* CCARM 1A023(Kan$^R$) | *P. aeruginosa* CCARM 2206(Amk$^S$) | *P. aeruginosa* CCARM 2178(Amk$^R$) |
| Pseudodi- | 3 | 128 | NA | 128 | NA | NA | NA |
| saccharides | 9 | 128 | NA | 128 | NA | NA | NA |
| | 4 | 64 | NA | 64 | NA | 128 | NA |
| | 10 | 64 | NA | 64 | NA | 128 | NA |
| Pseudotri- | 6 | 16 | NA | 16 | NA | 64 | NA |
| saccharides | 12 | 16 | NA | 16 | NA | 64 | NA |
| | 5 | 128 | NA | NA | NA | NA | NA |
| | 11 | NA | NA | NA | NA | NA | NA |
| | 7 | 2 | NA | 4 | NA | 32 | NA |
| | 8 | 2 | NA | 4 | NA | 16 | NA |
| | 13 | 128 | NA | 128 | NA | NA | NA |
| | 14 | 128 | NA | 128 | NA | NA | NA |
| AHBA- | 15 | 128 | 64 | 128 | 32 | ≤0.25 | NA |
| pseudotri-saccharides | 17 | 16 | 16 | 32 | 16 | 0.25 | 64 |

MIC: minimum inhibitory concentration. Type strains and clinically isolated strains were obtained from ATCC (American Type Culture Collection, USA) and CCARM (Culture Collection of Antimicrobial Resistant Microbes, Republic of Korea), respectively.
Kan$^S$ and Kan$^R$ represent the kanamycin-sensitive strain and the kanamycin-resistant strain, respectively. Amk$^S$ and Amk$^R$ represent the amikacin-sensitive strain and the amikacin-resistant strain, respectively.
NA represents no activity at 128 µg/mL.

Figure 7:
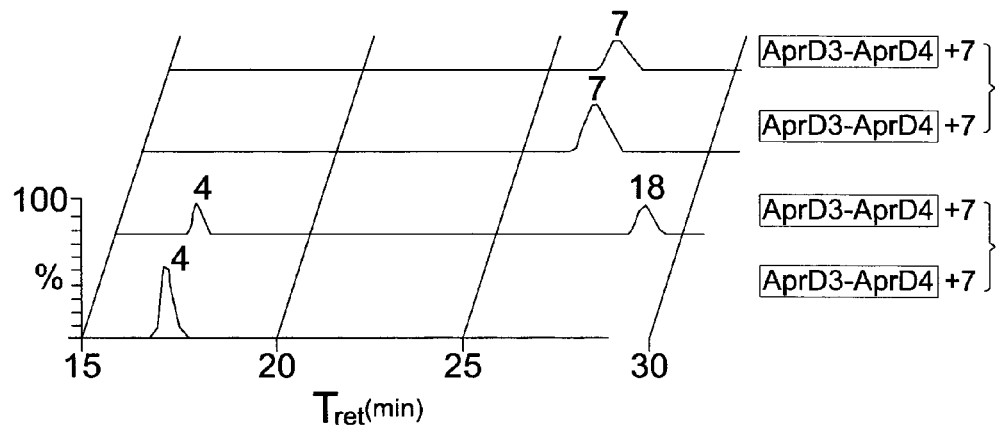
FIG. 7 shows the results of HPLC-ESI-MS/MS analysis of compounds 16 and 18 produced from in vitro reactions using cell-free extracts of recombinant *S. venezuelae* strains expressing aprD3-aprD4 gene pair. Each box represents the cell-free extract obtained from the recombinant host expressing aprD3-aprD4 gene pair, and black-framed boxes indicate boiled cell-free extracts as controls.

*brarius* containing tobM2 as a second glycosyltransferase encoding gene converted compound 18 into compound 16, but the cell-free extract of *S. kanamyceticus* did not (FIG. 7). Therefore, the inventor have constructed the glycosyltransferase encoding genes nemD, tobM2, and aprD3-aprD4 and a new strain (KABΔfnΔet$_2$a) expressing compound 7 biosynthetic gene and produced compound 16 (0.4 mg/l, 0.8 µM) (FIGS. 5B and 5C). The cell-free extracts of the strain expressing aprD3-aprD4 converted compound 4 into compound 18, but did not convert compound 7 into compound 16, which means that these enzymes are active only to pseudo-disaccharides (FIG. 7).

In one embodiment of the present invention, antibacterial spectra against kanamycin intermediates and analogs produced by the present invention were measured. Typical gram-negative strains (*E. coli* and *Pseudomonas aeruginosa*) and four clinically isolated strains were employed to check the antibacterial spectra (See table 2).

Among the pseudodisaccharides, the 6'-amino compounds 4 and 10 were more active than the 6'-hydroxy derivatives 3 and 9 against kanamycin-sensitive *E. coli* strains. Compared with compounds 6 and 12 containing 6'-hydroxy group, their 6'-amino counterparts 7 and 8 were more active against kanamycin-sensitive test strains. In addition, the 3''-amino compounds 6, 7, 8, and 12 showed increased activity against the test strains when compared with the corresponding 3''-hydroxy derivatives 5, 13, 14, and 11. Therefore, when C-6' and/or C-3'' hydroxyl group of kanamycin were aminated, the antibacterial activity was increased, which was consistent with the previous study.

The inventors have constructed 3D models of glycosyltransferases such as KanF and NemD. The 3D models were generated by homology modeling using the crystal structure of the MshA as a template. These enzymes shared over 40% overall sequence similarity, respectively. Critical residues and their interactions were preserved in both strongly supporting conserved catalytic association mechanisms.

To gain insight into the catalytic mechanism, the simulations aimed at the preparation of KanF/NemD complex with glycosyl-donors/acceptor were repeated. First, the inventors performed a docking of the glycosyl-donors (UDP-Glc and UDP-GlcNAc) to the putative substrate binding site in both glycosyltransferases KanF and NemD using AutoDock, respectively. Secondly, the glycosyl-acceptor (compound 1) was docked into the putative glycosyl-acceptor binding site of each glycosyltransferase/glycosyl-donors complex using CDOCKER and deeply docked into the Glc or GlcNAc area, thus making ideal interactions with their glycosyl-donors and the surrounding residues of each glycosyltransferase.

The distance between the C1 atom of the glycosyl-donors and O3 atom of compound 1 fluctuated only within very narrow limits (~3.0 Å). The total energy of the [KanF or NemD/glycosyl-donors/compound 1] complex was stabilized and remained stable during the simulation. The radius of gyration for the complexes was found to be stable at roughly 20 Å throughout the simulation, suggesting that the presence of compound 1 in the complexes induce the protein to adopt more compact form compared to the proteins in the absence of compound 1. There is a large hydrophilic pocket between two domains of glycosyltransferase KanF (or NemD). The pocket is formed by glycosyl-donor neighboring hydrophilic residues such as Glu14 (Glu41), Gln19 (Gln46), Gln20 (Gln47), His88 (His115), Tyr110 (Tyr137), Thr111 (Thr138), Asp117 (Asp204), Lys218 (Lys245), Asn272 (Asn299), Glu292 (Glu319), Glu293 (Glu320), Ser297 (Ser324), and Glu300 (Glu327). Analysis of hydrophilic-hydrophilic contact in the docked structure showed that these residues are playing a crucial role in the interaction. The sugar groups of glycosyl-donors/compound 1 would interact with hydrophilic residues of the binding pocket. The uracil moiety of both glycosyl-donors forms hydrophobic interactions with Gly243 (Gly270), Phe269 (Phe296), and Ile275 (Ile302), eral hydrophilic groups as described above, thus their hydrogen bond interaction with glycosyltransferases as well as solvent molecules at the active site is important for them to bind tightly with both KanF and NemD. The number of hydrogen bonds between KanF and UDP-Glc (~5) is larger than that between KanF and UDP-GlcNAc (~2), whereas the number between NemD and UDP-Glc (~3) is smaller than that between NemD and UDP-GlcNAc (~6), indicating that UDP-Glc binds more tightly to KanF than does UDP-GlcNAc to NemD.

The calculated free energies of UDP-Glc and UDP-GlcNAc binding to KanF and NemD is −42.2, −47.3, −41.4, and −46.7 kJ/mol, respectively (See table 3).

TABLE 3

Average binding free energies(kJ/mol) between glycosyl-donors and surrounding residues of KanF and NemD during molecular dynamics simulation.

|  | KanF + UDP-GlcNAc | KanF + UDP-Glc | NemD + UDP-Glc | NemD + UDP-GlcNAc |
|---|---|---|---|---|
| $\left\langle E\dfrac{vdW}{enz}\right\rangle$ | −7.98 ± 0.59 | −7.13 ± 0.17 | −8.07 ± 0.24 | −7.45 ± 0.40 |
| $\left\langle E\dfrac{vdW}{enz+sub}\right\rangle$ | −42.09 ± 0.39 | −35.04 ± 0.84 | −43.90 ± 0.38 | −41.95 ± 0.08 |
| $\left\langle E\dfrac{Elec}{enz}\right\rangle$ | −258.33 ± 1.65 | −284.48 ± 1.47 | −253.13 ± 1.34 | −277.01 ± 1.83 |
| $\left\langle E\dfrac{vdW}{enz}\right\rangle$ | −329.18 ± 0.47 | −367.88 ± 0.48 | −321.53 ± 0.74 | −356.63 ± 0.18 |
| $\left\langle E\dfrac{vdW}{enz+sub}\right\rangle$ | −42.25 ± 1.15 | −47.28 ± 1.82 | −41.37 ± 1.18 | −46.71 ± 1.09 |

* The binding free energy (ΔG)) calculation was based on the molecular dynamics simulation;

$$\Delta G = 0.2\left(\left\langle E\dfrac{vdW}{enz-sub}\right\rangle - \left\langle E\dfrac{vdW}{enz}\right\rangle\right) - 0.5\left(\left\langle E\dfrac{Elec}{enz-sub}\right\rangle - \left\langle E\dfrac{Elec}{enz}\right\rangle\right)$$

wherein < > denotes averages of the van der Waals (wdW) and electrostatic (Elec) interactions between the substrate (sub) such as UDP-Glc and its surrounding residues in enzymes (enz) such as KanF and NemD. 0.2 and 0.5 are scaling factor for wdW and Elec, respectively.

whereas their ribose moieties build the hydrophilic interactions with Ser297 (Ser324), and Glu300 (Glu327). The hydrophilic contact between compound 1 and Tyr110 (Tyr137) is strong because the phenolic group of Tyr is moved somewhat inward or outward from its original position as compound 1 which is located above the phenolic group tries to get closer to Tyr110 (Tyr137). However, Leu89 (Leu116) make a strong hydrophobic interaction with compound 1 which doesn't move much at all. The amino group at C3 position in compound 1 interacts with the Asp177 (Asp204) which allows the dissipation of the delocalized negative charge of compound 1. The hydroxyl group at C6 position in compound 1 make hydrophilic interactions with His88 (His115), whereas the ring moiety of compound 1 makes hydrophobic interactions with Gly16 (Gly43) and Val17 (Val44). The Glc or GlcNAc part in the glycosyl-donor is anchored to a pocket formed by Glu292 (Glu319), Glu293 (Glu320), and Leu294 (Leu321), proposing that these residues might play a critical role in the stability of those complexes. The sugar parts of glycosyl-donors stack against between the carboxyl moieties of Glu292 (Glu319) and Glu293 (Glu320). Leu294 (Leu321) is located at almost the center of hydrophobic and hydrophilic interaction with sugar moiety.

The inventors have performed the molecular dynamics and binding free energy analysis. The glycosyl-donors have sev- The inventors have discovered that the substrate-flexible glycosyltransferase KanF synthesizes compounds 9 and 2 by taking both UDP-Glc and UDP-GlcNAc as cosubstrates for attachment to compound 1. The discovery of the structure of compound 9 indicated that KanF is a glucose transferase as well as an N-acetylglucosamine transferase. The activity of this glycosyltransferase has not been known in the biosynthesis of aminoglycoside. Moreover, compound 9 is converted into compound 10 in the same way as compound 3 is converted into compound 4 by KanI-KacL. KanI-KacL also convert compounds 6 and 12 into compounds 7 and 8, respectively. The second glycosyltransferase KanE also shows remarkable substrate flexibility toward the glycosyl-acceptor and produces compounds 6, 7, 12, and 8, respectively by transferring UDP-Kns to compounds 3, 4, 9, and 10. KanE also takes UDP-Glc as the glycosyl-donor and transfers UDP-Glc to the pseudodisaccharide, thereby producing compounds 5, 13, 11, and 14 (FIGS. 2 and 3).

The method of directly producing AHBA-binding kanamycin using the recombinant strain of the present invention is first discussed as the direct fermentative production of the semi-synthetic aminoglycoside.

Moreover, compound 17 (1-N-AHBA-kanamycin X) as a new aminoglycoside compound produced by the present invention has strong antibacterial activity against all kanamycin and amikacin-resistant test strains. The unique structural difference between compound 15 and 17 is a functional group attached at C-6' position (FIG. 5C), which indicates that compound 17 is active against bacteria having resistance to compound 15 by removing the 6-amino group which acts as a target of aminoglycoside 6-acetyltransferase. Another advantage of compound 17 is the reduced toxicity due to the reduction in the number of amino groups.

Furthermore, the in vivo production of compound 16 by a modified pathway is more economical than the conventional method using hydrolysis of 6"-O-carbamoyltobramycin which occupies 9% of the total nebramycin factors produced by S. tenebrarius.

MODE FOR THE INVENTION

Hereinafter, the present invention will be described by way of examples in detail. However, the following examples are provided to facilitate the understanding of the present invention, and the present invention is not limited to or by the following examples.

Example 1

Preparation of Materials

Standard kanamycin, kanamycin B, neomycin, paromomycin, tobramycin, and amikacin were purchased from Sigma (USA). 2-mercaptoethanol, phenylmethylsulfonyl fluoride (PMSF), phenol/chloroform/isoamyl alcohol (25:24:1), uridine 5'-diphospho-D-glucose (UDP-Glc), and glass beads (150 to 212 μm) were also purchased from Sigma. Heptafluorobutyric acid (HFBA) was obtained from Fluka, and HPLC-grade acetonitrile, methanol, and water were obtained from J. T. Baker. 2-deoxystreptamine (2-DOS, compound 1) and UDP-2-N-acetyl-D-glucosamine (UDP-GlcNAc) were purchased from GeneChem (Republic of Korea). Cation solid-phase exchanger (OASIS MXC SPE, 3 mL/60 mg) and vacuum manifold were purchased from Waters. The culture medium components, soybean meal, yeast extract, and malt extract were acquired from BD Science (USA).

Paromamine and neamine were prepared from paromomycin and neomycin, respectively, by methanolysis. UDP-2-D-glucosamine (UDP-GlcN) was prepared by enzymatic reaction of UDP-D-glucose pyrophosphorylase with glucosamine-1-phosphate and uridine 5'-triphosphate (UTP). Escherichia coli DH10B and plasmid Litmus 28 (New England Biolabs) were used for routine subcloning. High-copy number E. coli-Streptomyces shuttle vector pSE34 containing the strong ermE* promoter plus a thiostrepton resistance marker was used as an expression plasmid.

Example 2

Culture of Strains

The recombinant strains of S. venezuelae were grown in liquid R2YE at 30° C. for preparation of protoplasts, which were regenerated on R2YE agar medium supplemented with thiostrepton (30 μg/ml). The E. coli strains used for subcloning were grown in LB medium supplemented with ampicillin (50 μg/ml) to select for plasmids.

For production of kanamycin biosynthetic intermediates and their analogs, S. venezuelae strains expressing the biosynthetic candidate genes were cultivated at 30° C. for 4 days in one liter of baffled Erlenmeyer flasks containing 300 mL of R2YE medium supplemented with thiostrepton (25 μg/ml). S. kanamyceticus ATCC 12853 was grown at 30° C. for 5 days in liquid ISP2 (0.4% yeast extract, 1.0% malt extract, and 0.4% glucose), and S. tenebrarius ATCC 17920 was grown at 30° C. for 5 days in fermentation medium (2.0% glucose, 2.0% soluble starch, 4.0% soybean meal, 0.5% yeast extract, 0.5% $CaCO_3$, and 0.4% $MgSO_4 7H_2O$, pH 7.0).

To check the antibacterial spectra of kanamycin biosynthetic intermediates and their analogs, a total six kinds of Gram-negative bacteria such as kanamycin-sensitive ($Kan^S$) E. coli ATCC 25922, kanamycin-resistant ($Kan^R$) Pseudomonas aeruginosa ATCC 27853, $Kan^S$ E. coli CCARM (Culture Collection of Antimicrobial Resistant Microbes, Korea) 1A020, $Kan^R$ E. coli CCARM 1A023, amikacin-sensitive ($Amk^S$) P. aeruginosa CCARM 2206, and amikacin-resistance ($Amk^R$) P. aeruginosa CCARM 2178 were used.

Example 3

Cloning and Construction of Expression Plasmids and Recombinant S. Venezuelae Strains An engineered strain of S. venezuelae, which is deficient in biosynthesis of the endogenous deoxysugar thymidine 5'-diphospho (TDP)-D-desosamine, was used as a heterologous host. A gene replacement plasmid, pYJ188, was introduced into protoplasts of S. venezuelae YJ003 mutant for deletion of the kanamycin modifying gene (aphII) by a replicative plasmid-mediated homologous recombination. Several double crossover mutants were identified on the basis of their phenotypes of kanamycin sensitivity and their genotypes by Southern hybridization.

DNA fragments containing a variety of kanamycin biosynthetic genes were amplified from pSKC2 by PCR with specific deoxyoligonucleotide primers (See table 1). The DNA fragments encoding NemD, GtmG, AprD3, AprD4, TobM1, and TobM2 were obtained by PCR-amplification using genomic DNA of S. fradiae ATCC 10745, Micromonospora echinospora ATCC 15385, and S. tenebrarius ATCC 17920, respectively. DNA fragments containing btrI, btrJ, btrK, btrO, btrV, btrG, and btrH required for S-4-amino-2-hydroxybutyric acid (AHBA) biosynthesis and transfer were PCR-amplified using genomic DNA of Bacillus circulans NR3312 as a template. Each pair of primers contained several restriction sites to facilitate subcloning of each DNA fragment.

PCR was performed using Pfu polymerase (Fermentas) under the manufacturer's recommended conditions. All PCR products were cloned into Litmus 28 and sequenced to confirm their authenticity.

For expression of 2-DOS biosynthetic genes, PCR-amplified fragments containing kanA-kanB and kanK were digested with BamHI/SpeI and XbaI/HindIII, respectively, and simultaneously ligated with pSE34 which had been cut with BamHI and HindIII, thus generating pDOS. Plasmid pDOSf (kanA-kanB-kanK-kanF-gtmF-gtmK-gtmL) was constructed to express kanF along with 2-DOS biosynthetic genes by ligating the SpeII HindIII-digested DNA fragment of kanF with the XbaI/HindIII fragments of resistance gene set (gtmF-gtmK-gtmL) isolated from pYJ489, and inserting into pDOS as an XbaI/HindIII fragment.

All subsequent cloning steps for construction of plasmids pPAR, pPARcd, pPARil, pKCXΔcΔd, pKCX, pKABΔcΔd, pKAB, pDOSn, pDOSt₁, pDOSg, pKCXΔfn, pKCXΔft₁, pKCXΔfg, and pKABΔfn were performed using the compatible cohesive ends of SpeI and XbaI sites.

For the direct fermentative production of 1-N-AHBA kanamycins, plasmid Litmus 28 containing btrG-btrH was digested by SpeI/SnaBI and ligated with the DNA fragment btrI-btrJ that had been cut by XbaI/SnaBI. The resulting plasmid carrying btrG-btrH-btrI-btrJ was subsequently ligated with the DNA fragment containing btrK-btrO-btrV in the same manner. Then, the plasmid containing btrG-btrH-btrI-btrJ-btrK-btrO-btrV was digested by XbaI/SpeI and transplanted into the XbaI site of pKCX and pKAB (See table 2) to generate pKCXb and pKABb, respectively. The correct orientations of the DNA fragments containing btrG-btrH-btrI-btrJ-btrK-btrO-btrV in the pKCXb and pKABb were confirmed by restriction fragment analyses.

Next, plasmid pKABΔfna and pKABΔfnΔet$_2$a were constructed in attempt to produce 3'-deoxykanamycins in vivo. The plasmid Litmus 28 containing aprD3 was digested by SpeI/HindIII and combined with the XbaI/HindIII DNA fragment containing aprD4. The plasmid containing aprD3-aprD4 gene set was ligated with the XbaI/HindIII DNA fragments containing nemD-kanE-kanC-kanD-kanI-kacA-kacL-gtmF-gtmK-gtmL. The resulting plasmid was moved into the XbaI/HindIII sites of pSE34 containing kanA-kanB-kanK (pDOS) to generate pKAB fna. Plasmid pKABΔfnΔet$_2$a was equivalent to pKABΔfna supplemented with tobM2 instead of kanE.

To prepare the cell-free extract of *S. venezuelae* for functional assignment of each kanamycin biosynthetic gene products, DNA fragments containing kanF, kanE, kanI-kacL, kanC-kanD, and aprD3-aprD4 were transplanted into pSE34 as XbaI/HindIII fragments, thus generating pKanF, pKanE, pKanI-KacL, pKanC-KanD, and pAprD3-AprD4, respectively. All resulting plasmids were then transformed into an engineered strain of *S. venezuelae*, thus yielding the corresponding recombinants.

Example 4

Isolation and Identification of Kanamycin Biosynthetic Intermediates and their Analogs HPLC was performed with a Spherisorb S5 ODS2 (250×20 mm, Waters) semi-prep column on the products of engineered recombinant strains in Example 3. The products were eluted with the same mobile phase used in HPLC-ESI-MS/MS analysis at a flow rate of 12 mL/min over a period of 150 min. The resulting eluent was fractionated into 3-mL portions that were monitored by HPLC-ESI-MS/MS to detect and characterize the presence of each kanamycin-related biosynthetic intermediate and analog. Fractions containing products of interest were pooled and extracted using OASIS MCX SPE followed by freeze-drying. $^1$H, $^{13}$C, and 2D $^1$H-$^1$H COSY NMR spectra were acquired using a Varian INOVA 500 spectrometer at 298 K. Chemical shifts were reported in ppm using trimethylsilyl-2,2,3,3-tetradeuteropropionic acid (TSP) as an internal reference. The assignment of each compound was carried out by comparison with previously assigned $^1$H and $^{13}$C NMR spectra, and NMR data processing was done using MESTREC (Magnetic Resonance Companion) software.

Example 5

Analysis of Kanamycin Biosynthetic Intermediates and Analogs

Kanamycin biosynthetic intermediates and their analogs produced by recombinant *S. venezuelae* strains expressing aminoglycoside biosynthetic genes were extracted from the fermentation medium using the OASIS MCX (Waters) SPE cleanup procedure and analyzed by HPLC-ESI-MS/MS.

Analytical HPLC-ESI-MS/MS was performed on the analytes in an XTerra MS C$_{18}$ column (50×2.1 mm, 3.5 µm, Waters). The analytes were eluted with acetonitrile and 10 mM heptafluorobutyric acid (Fluka) for 45 minutes. Quantification of the analytes was conducted using MS/MS in the multiple reactions monitoring mode. This was done by selecting the two mass ions set to detect a transition of the parent ion to the product ion specific to the selected analytes: compound 1, 163>84; compound 2, 366>163; compounds 3 and 10, 324>163; compound 4, 323>163; compounds 5, 12 and 14, 486>163; compounds 6, 8 and 13, 485>163; compound 7, 484>163; compound 9, 325>163; compound 11, 487>163; compound 15, 586>264; compound 16, 468>163; compound 17, 587>264; compound 18, 307>163; and compounds 19 and 20, 469>163. Three separate cultivations and extractions were performed.

Example 6

In Vitro Reactions to Analyze AprD3-AprD4 Activity

In vitro reactions to analyze the activity of AprD3-AprD4 pair on 3'-deoxygenation in the pseudodi- or tri-saccharide were carried out by supplementing 100 µM neamine or kanamycin B with the cell-free extracts from the recombinant host expressing aprD3-aprD4. After incubation at 30° C. for 2 hours, the reaction was quenched. The resulting supernatant containing the product of interest was extracted using OASIS MCX SPE, and then subjected to HPLC-ESI-MS/MS analysis. Independent experiments were carried out in duplicate, and the results are shown in FIG. 7.

Example 7

In Vitro Reactions to Analyze Glycosyltransfer Activity of KanF

Cell-free extracts of *S. venezuelae* were prepared by glass-bead homogenization. These cell-free extracts were suspended in a Tris buffer solution containing 100 mM TrisHCl (pH 7.6), 10 mM MgCl$_2$, 6 mM 2-mercaptoethanol and 1 mM phenylmethylsulfonyl fluoride (PMSF, Sigma), and each protein concentration was calibrated. The glycosyltransfer reaction by KanF was initiated by supplementing 100 µM 2-DOS together with 200 M UDP-Glc (Sigma), UDP-GlcNAc (GeneChem), or UDP-GlcN as cosubstrates to the cell-free extracts of the recombinant host expressing only kanF. 100 µM 6'-hydroxy pseudodi- and tri-saccharides 3, 6, 9, and 12 were mixed with the cell-free extracts of the recombinant host expressing kanI-kacL to measure the activity of KanI-KacL for C-6'-amination. The resulting cell-free extracts were incubated at 30° C. for 2 hours before quenching with ice-cold phenol/chloroform/isoamyl alcohol (25:24:1, Sigma) and then subjected to centrifugation at 18,000 g for 5 minutes. The supernatant containing the product of interest was extracted using OASIS MCX SPE, mixed with 100 µM water, and then subjected to HPLC-ESI-MS/MS analysis.

Example 8

In Vitro Reactions to Analyze KanC-KanD Activity

In vitro reactions to analyze the activity of KanC-KanD were carried out using cell-free extracts of two *S. venezuelae* strains expressing kanE or kanC-kanD. 200 µM UDP-Glc and 100 µM compound 3 or 4 were mixed with the cell-free extracts of the strains expressing kanE (or kanC-kanD) and incubated under the same conditions as Example 7 before quenching the reactions. After the resulting supernatant containing the product of interest was incubated together with the cell-free extracts of the strains expressing kanC-kanD (or kanE) at 30° C. for 2 hours, the reaction was quenched. The resulting supernatant was extracted in the above manner and then subjected to HPLC-ESI-MS/MS analysis.

Example 9

In Vitro Reactions Using Cell-Free Extracts from Wild-Type Strains of *S. kanamyceticus* and *S. tenebrarius*

Figure 8:
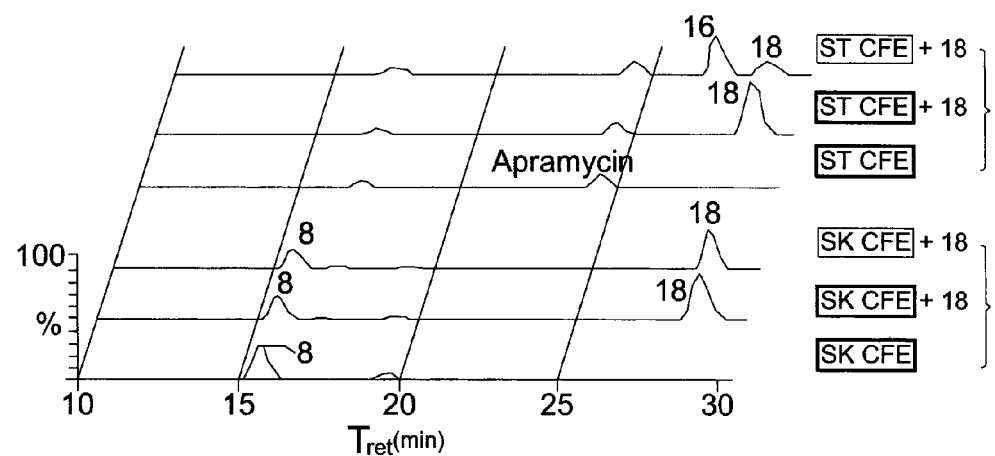
FIG. 8 shows the results of HPLC-ESI-MS/MS analysis of compounds 16 produced from in vitro reactions using cell-free extracts of wild strains of *S. kanamyceticus* and *Streptomyces tenebrarius*. Each box represents the cell-free extract obtained from *S. kanamyceticus* ATCC 12853 (SK CFE) and *S. tenebrarius* ATCC 17920 (ST CFE), and black-framed boxes indicate boiled cell-free extracts as controls.

In vitro reactions to determine the glycosyltransfer activities of KanE from *S. kanamyceticus* and TobM2 from *S. tenebrarius* on nebramine, were performed by supplementing 100 μM nebramine with the cell-free extract obtained from *S. kanamyceticus* (SK CFE) and TobM2 from *S. tenebrarius* (ST CFE). To minimize the presence of the kanamycin- or tobramycin-related congeners in the cell-free extracts of both wild-type strains, which might interfere with reactions, the cell-free extracts derived from glass-bead homogenization were further treated using OASIS MCX SPE pass-through as follows. At first, the cell-free extracts obtained from both wild-type strains were loaded onto each SPE cartridge, which was conditioned with methanol and water. Next, the pass-through from the cartridge was pooled, and the same step was repeated again. The above-mentioned cleanup procedures were all done in ice-cold conditions of about 4° C. The resulting cell-free extracts were incubated with compound 18 at 30° C. for 2 hours, and then subjected to the OASIS MCX SPE cleanup and HPLC-ESI-MS/MS analysis. Independent experiments were carried out in duplicate, and the results are shown in FIG. 8.

Figure 9:
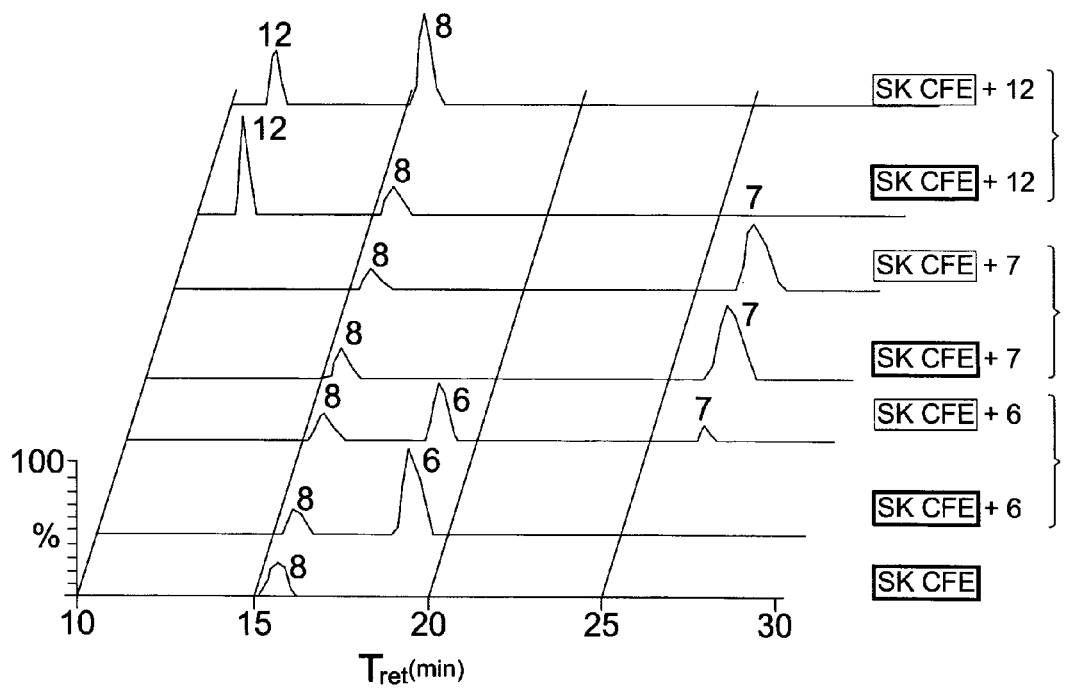
FIG. 9 shows the results of HPLC-ESI-MS/MS analysis of kanamycin pseudodisaccharides obtained from in vitro reactions using cell-free extracts of wild-type *S. kanamyceticus* strain. Each box represents the cell-free extract obtained from the *S. kanamyceticus* ATCC 12853 (SK CFE), and black-framed boxes indicate boiled cell-free extracts as controls.

Reactions to determine the conversion of compound 6, 7, or 12 into compound 8 were performed by supplementing 100 μM of compound 6, 7, or 12 with the cell-free extracts obtained from *S. kanamyceticus*. These cell-free extracts derived from glass-bead homogenization were further purified using OASIS MCX SPE pass-through as described above. After incubation at 30° C. for 2 hours, the reaction was quenched. The resulting supernatant containing the product of interest was extracted using OASIS MCX SPE, and then subjected to HPLC-ESIMS/MS analysis. Independent experiments were carried out in duplicate, and the results are shown in FIG. 9.

Example 10

Measurement of MIC of Kanamycin Biosynthetic Intermediates and Analogs

Minimum inhibitory concentrations (MICs) of various kanamycin-related pseudodi- and tri-saccharides and AHBA conjugated kanamycin analogs (except for compounds 16, 18, 19, and 20) were measured by broth microdilution according to the Clinical and Laboratory Standard Institute (CLSI, formerly NCCLS). As described in Example 2, gram-negative *E. coli* strains, *P. aeruginosa* strains, and clinically isolated strains were incubated in Mueller-Hinton broth (BD Science) at 30° C. Then, the aminoglycoside produced in the present invention was diluted 2-fold serially to give final concentration between 0.25 to 128 μg/ml. An aliquot of water was used as a negative control group. The growth of the strains was observed using the Labsystems Bioscreen C, and the minimum concentrations of the aminoglycoside diluted in the broth medium to inhibit the growth of the bacterial strains were measured.

Example 11

3-Dimensional (3D) Implementation for Glycosyltransferases Such as KanF and NemD Homology modeling of a couple of glycosyltransferases such as KanF and NemD was performed with MODELLER and optimized by FoldX using the atomic coordinates of MshA (PDB code: 3C48) as a template. The 3D structure models were assessed by VADAR program. Molecular docking was employed to determine the binding conformation of the glycosyl donors (UDP-Glc and UDP-GlcNAc) and acceptor (2-DOS), and energy-minimized and structure-optimized with Gaussian03 using HF/6-31G(d) basis set for molecular dynamics simulation.

The docking of the glycosyl donors and 2-DOS to glycosyltransferases was initially conducted according to the predicted topological binding sites by several algorithms. The automated docking was carried out by CDOCKER program (Accelrys, Inc.) based on the MMFF force field and AutoDock 4.0 program suite. The active site was defined with 6 Å radius sphere from the putative catalytic center of KanF and NemD. Each complex model was solvated with TIP3 water molecules in a cube box and ensured the whole surface of KanF and NemD protein with their glycosyl donors/2-DOS to be covered by a water layer with a thickness more than 12 Å The energy minimization for each complex was performed using the steepest descent algorithm, followed by the conjugate gradient in the CHARMM. Then, a 500-ps position restrained molecular dynamics was performed with the proteins and glycosyl donors/2-DOS using CHARMM package. Finally, a 3 nanoseconds molecular dynamics was started by taking initial velocities from a Maxwellian distribution at 300 K. Solvent and glycosyl donors/2-DOS were independently, weakly coupled to a temperature bath with a relaxation time of 0.1-ps. The system was also isotropically, weakly coupled to a pressure bath at 1.0 atm with a relaxation time of 0.5 picoseconds and an isothermal compressibility of $0.5 \times 10^{-3}$/bar. Long-range electrostatics was calculated by the particle-mesh Ewald method. Short-range van der Waals and coulombic interactions were cut off at 0.1 Å. All bond lengths were constrained using the SHAKE algorithm, and the time step was set to 0.002 picoseconds. The binding free energies between the glycosyl donors and KanF (or NemD) were calculated using the linear interaction energy method using default parameters.

While the invention has been shown and described with reference to certain exemplary embodiments thereof, it will be understood by those skilled in the art that various changes in form and details may be made therein without departing from the spirit and scope of the invention as defined by the appended claims.

[Accession Nos.]
KABΔfn strain: KCTC11725BP
KABΔfnΔet$_2$a strain: KCTC11726BP
KCXb strain: KCTC11727BP
KABb strain: KCTC11728BP

INDUSTRIAL APPLICABILITY

According to the present invention, a kanamycin-producing *Streptomyces* species bacterium, a method of effectively producing kanamycin, and a new kanamycin compound produced by the same are provided.

The invention claimed is:

1. An isolated compound of formula 1 or a pharmaceutically acceptable salt thereof:

[formula 1]

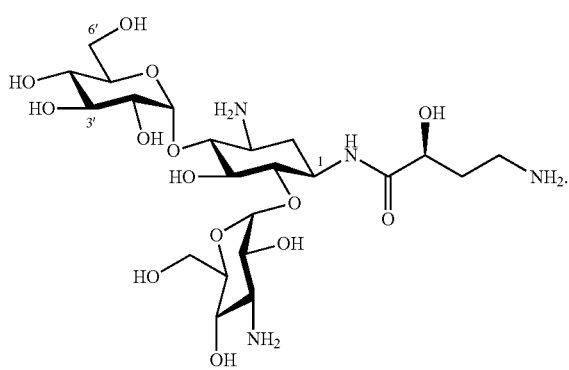

2. A pharmaceutical composition comprising the isolated compound of formula 1 or a pharmaceutically acceptable salt thereof, according to claim 1, and a pharmaceutically acceptable excipient.

3. A method of treating a bacterial infection or a viral infection in a patient comprising administrating to the patient a composition comprising the isolated compound of formula 1 or a pharmaceutically acceptable salt thereof, according to claim 1.

4. The method of claim 3, wherein the bacterial infection is a Gram-negative bacterial infection.

5. The method of claim 3, wherein the bacterial infection is a *Pseudomonas aeruginosa* infection or an *Escherichia coli* infection.

6. The method of claim 5, wherein the *P. aeruginosa* is amikacin-resistant *P. aeruginosa*.

* * * * *

SEQUENCE LISTING

<160> NUMBER OF SEQ ID NOS: 62

<210> SEQ ID NO 1
<211> LENGTH: 825
<212> TYPE: DNA
<213> ORGANISM: Micromonospora echinospora

<400> SEQUENCE: 1

```
atgacgacat ctgcgcctga ggaccgtatc gaccaggtcg agcaggccat caccaagagc      60
cggcgctacc agacggtggc cccggccacc gtgcggcgcc tggcccgggc tgccctcgtc     120
gccgcgcggg gcgacgtgcc ggacgcggtg aagcgcacca agcgcgggct gcatgagatc     180
tacggggcct tcctgccgcc cagcccgccc aactacgcag cgttgctgcg gcagctcgac     240
tccgctgtgg acgccggtga cgacgaggcg gtccgggcgg ctctgcgccg cgcgatgtca     300
gtgcatgtgt ccactcgtga gcgattgccg cacctggcgg agttctacca ggagatcttc     360
cgtcacgtgc cccagcccaa cacgctgcgt gacctcgcct gtggcctcaa tccgctggcc     420
gctccctgga tgggcctgtc ggaccagacc gtctacgtcg cctccgacat cgacgcccgg     480
ctgatcggct tcgtggacgc cgccctgacg aggctgggcg tcgcgcaccg tacgagcgtg     540
gtcgacctcc tcgaggaccg ccttgacgag ccgaccgacg tcacgctatt gctgaagacg     600
ctgccctgtc tggagactca gcgacgaggc tccggctggg aagtgattga cattgtcaac     660
tcgccgatta tcgtggtaac cttcccgacc aagtctctcg gtcagcgatc gaaggggatg     720
tttcagaact attcacaaag ttttgagtcc caggccagag aacggtcgtg ccgaattcag     780
cgactggaga tcggcaacga gctgatttac gtcattcaga aatag                     825
```

<210> SEQ ID NO 2
<211> LENGTH: 1407
<212> TYPE: DNA
<213> ORGANISM: Micromonospora echinospora

<400> SEQUENCE: 2

```
atgtctgaca cggccaaaca agcgaccggc gcggaggtca agcagcccgg cgcagcgggt      60
cccagccgac cgggactcgc gctgacccgt ctggcctcct gtgcgttgat gatcgtcctc     120
gactcgacgg tggtctacgt cgccctgccg cagatccagc agagcctcga ggtgagcgcc     180
accgggctgg tctgggtggt caacgcgtac gccctggcgt tcggcggtct gatgctgctc     240
ggcggccggg ccggcgacat cgtcggccag cggcggatcc tcctcgtcgg gctggcggtc     300
ttcggcgtcg cctcgctgat ctgcggtctg gcgacctcgc cggagatgct gatcggtgcc     360
cgtgccctcc aggggatcgg ggccgcgctg gtcgccccga cgtcgctctc gctgattccg     420
atcaacttca ccgacaacgc ggcccggaac aaggcgatcg gtgtctacac cggcatcgcc     480
gcggccggcg gcacgctcgg cctgatcctc ggcggggtgc tcagcgacgc cgcctcctgg     540
cgctgggtgt tcttcatcaa cgtgccggtg gtcgcgctgg tgctcctgct cgcgccgcgc     600
gtcctgcgcg agagccagcc gcagcgcggc tcgttcgaca tcgtcggggc ggtgacctcg     660
accggtgcga tggtcgccct ggtgtacgcg ctcgtccgca cctcgaccaa gggttggggc     720
gacccggtcg tcctggcctg cctcgccgtg gcggccgtcc tgttcaccgt gctgatcctg     780
gccgagcgtc gggcccggca gccgctgctg ccgctgcggc tgttcgccga ccgggtccgg     840
gccagcggct tcgtcaccct gctgttcttc ccggccgcct tcgccggcat gttcttcttc     900
ctcacccagt acttccaggg ggtgtggagc tactccgcgc tgcgtaccgg gttcgccttc     960
atcccggcgg cggtcctggt cctggtcgcc gcgatcctga gcggacagct ggtacccaag    1020
```

```
ctcggtccga gcgtcgtggc cgggatcggc gcgctgctca ccacgctcgg gatgatctgg    1080
ctcacccaga tctccgccga cggcggctac gtcacctcgc tgctcggtcc gctggcgatc    1140
gccggtttcg cgccggcct gatctactcg tcggtgaccg cctcgatcat gtccaacgtg    1200
gcgccggagg tgaccggcgc ggcgtccagc gtgttgcagg cggtccagca gatcggtccg    1260
gcgctgggac tggccgtgct ggtcaccgcg gcgggcacgc ccgccgaccc ggtcgagggg    1320
atgcgtaggg cgttctgggt ggctgccgtc atcgccgcgc tgccggccgt cctcgccctg    1380
ttcaaccgtc ggtcgcgtac cgagtga                                        1407
```

<210> SEQ ID NO 3
<211> LENGTH: 894
<212> TYPE: DNA
<213> ORGANISM: Micromonospora echinospora

<400> SEQUENCE: 3

```
gtgccggccg gtgaaccggc accggccacc cggccggagc cggagtcggc catcctgccg     60
gagccggccg cggccgtgcc gtcgccgccg ccggagtcac ccgccgtgca gaaggtgatc    120
gcccggctca ccgccgcggc caagtaccgt gacgtgcacc cggagaccgt cgccgacctg    180
gtccggcggg agggtcgggc caccggggac gccgccgagc tggaacggcg ggtccgggcc    240
cggctgcaca aggtcgccgc cctgcacctg ctcaccgccc ggccggcggc gctgcgcaag    300
gcgctggacc gggccgacct cgacgacccg cagtcccggc gggactggtg ccggcaggtg    360
ctggccgggc acttctccac cgccgaacgc ctgcccgacc tggacacctt ctacccgacc    420
ctgttcgggc tggtgccgcc gccggagacg gtggccgaca tcgcgtgcgc gctgaacccg    480
ttcaccgtgc cctggctgcg ggaggtgagc gacgcccgct acgtcggcta cgacttcaac    540
gcgacgttcg tggagctggg caacgcgttc ctcgcccgga cccatccgga gtgcgagatc    600
cggcacgagg aggtgctcac cgacggccac cgggtgagcg ctgacctggg gttgctgctc    660
aagacgtacc actgcatgga gggacgccgg cccggcgccg ggctggcgct ggtcgaccgg    720
ctggcgtgcc ggcacgtggt ggtgtcgttc cccaccgggg ccatgaacgg ccgggcggcg    780
gtcttcgtgc cccgtcacgt ggaggagctg gccgagctgg cccgcgaccg gggatggagc    840
tggtcgcggg ccactctggc gtccgaggac ctggtggcga tccacaagga gtga          894
```

<210> SEQ ID NO 4
<211> LENGTH: 1176
<212> TYPE: DNA
<213> ORGANISM: Micromonospora echinospora

<400> SEQUENCE: 4

```
gtgggcggta tgcaggtgca gatcctggcg ttgtcccgca gcctggccag ggcgggcgtc     60
gaccagctcg tgctgaccct gggctttccg gggttgccgc cgacgaagca gatcgagccg    120
ggcctgaccg ttcgtatcgc ccgggtgtcc ctgcccagca tccgttccga gatcactgga    180
ttggtcggcc tgggacaggc atggttgatc ggaaccatcc gggagtgcct ccggttgcgt    240
cgcggtgact ggcgccccga tctcgtccac gtgcacgccg acggccagat ctggccactg    300
gtcgcgggtc ggatcgccgc ccggatcctg gcgtgccgt acgtgctcac cctgcactgc    360
tcccggctct ccgtctacca gccgatgtcg gcggtggacg cgatggcgca ccgcctggtc    420
acccaggcgg aacgacaggc gctgcgctcc gccgccgggg tcagcaccct gaccgccgc     480 accgccgacg tggtgagcgc cgcgaccggt ctggaccgct ctgccatcgt ggtcaacccg    540
```

| | |
|---|---|
| gacgcggtcg acatcacccc ggccacgccc gccgaggcgg cggcgttcgc gcagcggtac | 600 |
| ggcctgaccg gccgccggcc gctcatcggc tacatcggcc gggtcgccca cgagaagggc | 660 |
| tggccggacc tgctccgcct ggccgaactt ctggacgacc tctccccgac cttcctcgtc | 720 |
| gtcggtgacg gcccccagcg ggaacggatg gaacgggaga tcgccgaggc cggtcgcgcg | 780 |
| caccagttcg tggtgaccgg tttcctcccg cacgaccagg tgccggccgc tctcgcgctg | 840 |
| gtggacaccc tggtcatgcc ctcgatccac gaggaactcg ggggcagcgc gatcgaggcg | 900 |
| atcatgacgg gcaccccggt cgccgcctac gcggtcgggg gactgcgcag caccatcggc | 960 |
| tcggcctgcc ccgacctgct cagcgagccc ggcgacgtac gcggactcgc cgacgtcgtc | 1020 |
| cggcacgtcc tgaccgaccg ggacgcggtg gtcgcgcaga tccacgccgc gcagaccagc | 1080 |
| accgccagca ccttcgacgt cgccgccacc cgggaccgga tgatcgactg ctaccgcgcc | 1140 |
| gccctcgccg gggccggggc ggcgagcggg aagtga | 1176 |

<210> SEQ ID NO 5
<211> LENGTH: 1173
<212> TYPE: DNA
<213> ORGANISM: Streptomyces kanamyceticus

<400> SEQUENCE: 5

| | |
|---|---|
| atgcaggtca ccaccatcac gatggatgac gtccagtatc cctaccgatt aggcacggac | 60 |
| tgcctcgacg gcatcgtcac gcgcctcggc gaactcggcg ccagccgcta cctgatcgtc | 120 |
| agcgacccca gggtcgccga gctgtacggg caggggctgc gcgaacggct cgcggagcag | 180 |
| gcgggacccg ccgagctgat cacccatgcc tcgggagaac agaacaaggg cctgcccgca | 240 |
| ctgcacgacc tggccgagga ggcgctgcgg cgcggcgccg accggcagag catcgtcgta | 300 |
| gcactcggcg gcggtgtcac cgggaacatc gcggggctgc tggccgcgct gctcttccgc | 360 |
| ggcatccgtc tggtgcacgt gcccaccacc gtggtggcca tgctggattc ggtgctctcg | 420 |
| ctcaagcagg ccgtgaacgc gggagtcggc aagaacctgg tcggcacctt ctaccagccc | 480 |
| gtcgaagtgc tcgccgacac cgccgatgctg cgcaccctgc cggtccgcga ggtcaggtcg | 540 |
| gggatgtgcg aggtggtgaa gaactcgctc gccatccgcc ccagcatgat cgaccagctg | 600 |
| tcggccgggc tgcgccccga cggccgctat cccgacgaca cgatgcactg gatcatctac | 660 |
| gagagcctgg ccgccaaggc ccaggtcacg gcgtacgaca gtacgagcg cggcgaggga | 720 |
| ctcatcctgg agtacgggca caccgtcggg cacgccgtgg agcactcctc gcagggagcc | 780 |
| gtgccgcacg gcgccgccgt cgcgctcggc atgatcgccg ccgcccaggt ctcccaccgg | 840 |
| gcgggctggg cctcggccga actcgtcgac ctgcaccggg agctcgtcgc caagaccggg | 900 |
| gtcgcgcggc gcatcccgtc cgacataccg ctctccgccg tcaggcaccg cctctccttc | 960 |
| gacaacaagc ggggctacct cccggcctcc gccgacacct atccgatggt gctgctcgaa | 1020 |
| tcccccggca aggtgctgcg cagcgagggc accgtcctga cggcggcgcc acgggacctg | 1080 |
| gtcgacgcgg tggtcgacga actcgcgaa ccccacggc ccgcggccgc gaggaccgac | 1140 |
| gacgccgcca ccgtcctcgg cggtgccggg tga | 1173 |

<210> SEQ ID NO 6
<211> LENGTH: 1284
<212> TYPE: DNA
<213> ORGANISM: Streptomyces kanamyceticus

<400> SEQUENCE: 6

| | |
|---|---|
| atgcccctgc aaagttcacg gcttgcggtc gacaacggaa ccccgtccg cggcaagccc | 60 |

```
tggccggtgt ggccgcagcc caccgacggc accctcgacg ccctctcccg cgtcctgcgt      120
tccggccgct gggccatcag cggcccctac cggggcgtgg agtcggccga acgccgcttc      180
gcccgccggt tcgccgacta ccaccgcatc gcccactgcg tgcccgcctc cagcggtacg      240
gcgagcctga tgctggccct ggaggcctgt ggcgtcggcg cgggagacga ggtcatcctg      300
cccggcgtca cctgggtcgc ctccgcctcc acggtggtgg gcgtcaacgc ggtgccggtg      360
ttcgccgaca tcgaccccga caccctctgc ctcgacccgg acgccgtcga ggcggccatc      420
accccggcca ccaaggcgat cgtcgtcgtc cacctctacg cggccgtcgc cgacctcacc      480
cgcctcaagg aggtggccga ccggcacggc atcgtgctca tcgaggactg cgcgcaggcc      540
cacggcgccg agttcgaagg ccacaaggtc ggcaccttcg gcgcggtcgg caccttcagc      600
atgcagcaga gcaaggtcct gaccagcggc gagggcggcg ccgccatcac cgccgacccg      660
gtgctcgccc gccggatgga cacctgcgc gcggacggcc gctgctaccg cgatcaggcg      720
ccgccctccg gccacatgga gctcgtcgag acgggcgagc tgatgggcag caaccgctgc      780
atctccgagt tccaggcagc ggtcctgacc gagcagctgg gcgaactcga ccggttcaac      840
gccctgcgac ggcacaacgc ggaactcctc gacgcgctgc tgaccgacgt cggataccgc      900
ccgcagcgca gcacgcccgg caccaccgcc cgcacgtact acacctacgt cgccgagctg      960
cccgacgcgg aactgcccgg cgcggacatc accaaggtca ccgaggcgct gaccgccgaa     1020
ctcggcttcc cggtggcacc ggcctactcg ccgctcaacg ccaacccct gtacgacccg      1080 gccagtcgca gccggttcgc cctcggaccg cagcacgaga agctcatcga ccccgcccga     1140
ttcgtgctcc cggtgagcgg ccgcctgacg cgtcggctcg tcaccttcca ccacgccgcc     1200
ctgctcggcg acgagtcgga catgagggac atcgcggaag cgttcaccaa ggtgctccag     1260
caccgggccg tcctggccgc ttga                                           1284
```

<210> SEQ ID NO 7
<211> LENGTH: 2064
<212> TYPE: DNA
<213> ORGANISM: Streptomyces kanamyceticus

<400> SEQUENCE: 7

```
gtgaaggcac tcgtgttcca cagccccgag aaggcgacct tcgaacagcg cgacgtcccc       60
actccccggc cgggcgaagc cctcgtccac atcgcgtaca actccatctg cggcagcgac      120
ctctcgctct accgcggtgt ctggcacggc ttcggctacc ccgtcgtgcc cggacacgag      180
tggagcggca ccgtggtcga gatcaacggc gccaacggac acgaccagtc gctggtcggc      240
aagaacgtgg tgggcgatct gacctgcgcg tgcgggaact gcgcggcctg cgggcgcggg      300
accccggtgc tctgcgagaa cctccaggaa ctcggcttca ccaaggacgg cgcctgcgcc      360
gagtacatga ccatcccggt cgacaacctc cgcccgctgc cggacgcgct gtcgctgcgt      420
agcgcctgcc aggtcgaacc gctcgcgtg gcgctcaacg cggtcagcat cgcgggcgtc      480
gctcccggtg accgggtcgc cgtcatgggg ccgggggca tcggcctcat gctgatgcag      540
gtcgcgaggc atctcggcgg tgaggtgacg gtcgtgtccg aaccggtcgc gaacggtga      600 aggcactcgt gttccacagc cccgagaagg cgaccttcga acagcgcgac gtccccactc      660
cccggccggg cgaagccctc gtccacatcg cgtacaactc catctgcggc agcgacctct     720
cgctctaccg cggtgtctgg cacggcttcg gctaccccgt cgtgcccgga cacgagtgga     780
gcggcaccgt ggtcgagatc aacggcgcca acggacacga ccagtcgctg gtcggcaaga     840
```

```
acgtggtggg cgatctgacc tgcgcgtgcg ggaactgcgc ggcctgcggg cgcgggaccc      900
cggtgctctg cgagaacctc caggaactcg gcttcaccaa ggacggcgcc tgcgccgagt      960
acatgaccat cccggtcgac aacctccgcc cgctgccgga cgcgctgtcg ctgcgtagcg     1020
cctgccaggt cgaaccgctc gcggtggcgc tcaacgcggt cagcatcgcg ggcgtcgctc     1080
ccggtgaccg ggtcgccgtc atggggggccg ggggcatcgg cctcatgctg atgcaggtcg     1140
cgaggcatct cggcggtgag gtgacggtcg tgtccgaacc ggtcgccgaa cggcgcgcgg     1200
tcgccgggca gttgggcgcc accgagctgt gctccgccga gccggggcag ctggccgaac     1260
tcgtcgcccg cgcccccgag ctcacgcccc acgtggtcct ggaggcatcc ggctatccgg     1320
ctgcgctcca ggaggccatc gaggtggtca ggccgggcgg ccgcatcggc ctgatcggct     1380
accgggtgga ggagacggga ccgatgtccc cgcagcacat cgcggtcaag cgctgacccc    1440
tgcgcggctc gctgggcccc ggcggccgct tcgacgacgc cgtcgaactg ctcgcgaagg    1500
gcgacgacat cgcggtcgag ccgctgctca gccacgagtt cggcctcgcc gactacgcca    1560
ccgcgctcga cctggcgctg tcccgcacga acggcaacgt gcgctccttc ttcaacctgc    1620
gcgactaggc gcgcggtcgc cgggcagttg ggcgccaccg agctgtgctc gccgagccg    1680
gggcagctgg ccgaactcgt cgcccggcgc cccgagctca cgcccgacgt ggtcctggag    1740
gcatccggct atccggctgc gctccaggag gccatcgagg tggtcaggcc gggcggccgc    1800
atcggcctga tcggctaccg ggtggaggag acggaccga tgtccccgca gcacatcgcg    1860
gtcaaggcgc tgaccctgcg cggctcgctg ggcccggcg ccgcttcga cgacgccgtc    1920
gaactgctcg cgaagggcga cgacatcgcg gtcgagccgc tgctcagcca cgagttcggc    1980
ctcgccgact acgccaccgc gctcgacctg gcgctgtccc gcacgaacgg caacgtgcgc    2040
tccttcttca acctgcgcga ctag                                          2064
```

<210> SEQ ID NO 8
<211> LENGTH: 1164
<212> TYPE: DNA
<213> ORGANISM: Streptomyces kanamyceticus

<400> SEQUENCE: 8

```
atgcaggtac agatcctgcg gatgtcccgc gccctggccg agttgggggt gcgccagcag       60
gtgctcaccg tcggcttccc cggtctgccc agagtgcggc gcgactccga gaacctggtg      120
gtgcggatca ccagggcccc gctgcccagg ctgcgctcca ggatcaccgg cctggtcggc      180
ctcaaccagg cgtggctggc cgccgcgctc accgaatgcg tgaaactgcg gcgccgctgg      240
cccgccgacc tgatccaggt ccatctggac ggccagctct gggcgttgct cgcgggaccg      300
gtcgccgccc gctggtggg cgtgccgtac acggtcaccg tgcactgctc gcggctggcg      360
gtgtatcagc ccatgtccac cgtcgaccgc atccagcacc ccttggtgac cgccgtcgag      420
cgctgggcgc tgcgccgtgc ggccgggatc accacgctga ccgagcggac cgccacggtg      480
ctcgccgccg aactgggcgc ggcccagagg gtgatcgacg tggtgcccga cgcggtcgac      540
cccgatcggg ccgaggccgc gcccgccgag gtcgagcggc tgaagaagcg tttcggcctg      600
ccgcaggagg gcggtcccgt catcggattc gtcggccgga tcgcccacga aagggctgg      660
cgccacgccg tccaggcggt ggccgaactc gcggacgcgg gccgggactt caccttcctc      720
gtcgtcggag acggaccgca gcgggccgac atgagggcgg cggtggccga ggccggtctc      780
accgaccggt tcgtcttcac cgggttcctg cccaacgacg agatcccgcc gtgatgacc      840
gccctggacg tcctcctgat gccgtccgtg cacgaggagt tgggcggcag cgccgtcgag     900
```

```
gccatgctcg cgggaacgcc ggtggccgcc tacggggtcg gcggcctgtg cgacaccgtg    960
ggcaaggtga ccccgtcctt gctggccgcg cccggccagg tggccgaact cgcgcggacg   1020
gtcaagcggg tactcgacga tcccgcgccg gtcctggccg aattgcgtgc cggacgggag   1080
tggctcgcgg acgagttcgg tgtccaccac gcggccggtc tcgcgttggc ccactatgag   1140
cgggtactcg gcaaagaacg gtag                                          1164
```

<210> SEQ ID NO 9
<211> LENGTH: 750
<212> TYPE: DNA
<213> ORGANISM: Streptomyces kanamyceticus

<400> SEQUENCE: 9

```
gtgagggtcc tcctcgtctc cccccacccc gacgacatcg cgctgtcctt cggcggctgg     60
gtcgcggccc acgcccgcgg gctcgcggcc aagggctggc ggttcgacct gctgaccgtc    120
ttcggcacga ccctgtacgc gccccacagc ccgcgcgccg tcaccaagga ggccatcagc    180
acgctccggg agcgcgagga ccgcgactac gcgcgccgtc acgggctgcg gctgacctct    240
ctccggcagg aggactgctc ctgcctgggc atggacgacg aggaggagct catcgccccc    300
gaggcgaccg atcctcgccg ggccgccgtg cggcagctga tcgcggcggc gctcgccggg    360
gccgacctgg tcgtcgcgcc gctggctgtc ggcggccacg tggatcaccg catcgtccgc    420
accgcggtgc ggcagtcgct cggcgccacc ccctgcctct ggtacgagga cctgccgtac    480
gcgttggaga gccccgtcga ggtgccctcc gaccaccggc cctggctggt cgacatcagg    540
gggcacgagg cggccaagcg cgccgatctc gcgctgtacc gctcgcagat gaccgccgcc    600
gacacctccg aggtcctctc gtaccggccg gacggcgcgt ccgtcccgtg cgagcggctc    660
tggagttcgg cgggcttccc ccaggacctg gccgagcgga tggcactggc cacgctggcc    720
gccgtgacac ccgacaagga gtcgctatga                                    750
```

<210> SEQ ID NO 10
<211> LENGTH: 1170
<212> TYPE: DNA
<213> ORGANISM: Streptomyces kanamyceticus

<400> SEQUENCE: 10

```
atgggcggca tgcacctgct ggtgcgggcc ctggtcgagg agatggcggg ccgcggcgtc     60
ccgcaccggg tcctgacgat gtcaccgccc aaggtgccca aggacatcag gatcgggcag    120
cggatcaagg tgcacgcccg gcggctgccc gtgctgccca tcccctccga cctggagggg    180
tacttcggac tcgtcggcgc ctgggccaag ggcagcctgt tgtgggtgct gcgcaaccgc    240
aagcggctgc gccgggagat cggggcgcgg gtgcacgcgc actgcgacgg ctcgggcgcc    300
gcggccttct acccgtatct gatgtcccgg atcctcggcg tgccgctggt ggtccagatc    360
cactccagcc gctatctgag ccagcacccc accacgctct cgagcgggt gaccgacccg    420 atcgccaagt gggcggagcg gcacgccgtc cgcaaggccg ccgcggtcct gatgctcacc    480
gaccgggccc gcgacgagat gcggcgcaag gcccagctgc ccgcggagcg cgtgcaccgg    540
ctcgcgtacc tggccagcga ccagttcaag gacgccgaca ccgaggcgag gcgggcggaa    600
ctgcgggagc gctacggcct cgacgaccgc ccgatcgtgc tctacgtggg gcggatcgcc    660
gccgagaagg gcgtggagta ctacatcgag gccgcggccg aactgacccg caggggccgg    720
gactgccagt tcgtcatcgc cggggacggt cccgcccggc cggacctcga aaagctgatc    780
```

```
ggcgcccgcg ggctgcgcga ccgggtgacc atcacgggct tcatgtccca cgagttcatc    840
ccatccatga tctccctggg cgaactcgtg gtgctgccgt cccggtacga ggagctgggc    900
atcgtcatcc tggagtgcat gaccatgcgc aggccgctgg tcgcgcacga cgtgaacggc    960
gtcaacaagc tcatcgagga cggcaccacc ggaatcgtcg tacccccgtt caggaccccg   1020
gagatggccg acgccgtcga gcggctcctc gacgatccgg agctgcgcga gcggatggcg   1080
gagaacgccg ccccgctgcc cgccgccaag tactcgctct ccgcggcggg cgaccaactg   1140
gcgggcatct accgggagat cgggctgtga                                    1170

<210> SEQ ID NO 11
<211> LENGTH: 1080
<212> TYPE: DNA
<213> ORGANISM: Streptomyces kanamyceticus

<400> SEQUENCE: 11
atgggcgggg tgcacgccga ggtggtggcg gctcatcccg cgcccggct cgaagcggtg     60 cacgacctcg accccgccgc cgccaggac ctggccgagc ggttccgcgc cgagcgggcc    120
gagccctcct gggcggacct gctcgccgac cccgcgatcg acctgctcat catcaccacg    180
cccaacgggc tgcaccaccg gcaggcgccc gaggcgctgc gggcgggcaa gcacgtactg    240
gtggagaagc cgctcggtgt cacgccggag caggtggccg agctcgtcga actcgccgga    300
cggcacgacc gggtccttgc ccacggaagc aacttcgtgc acagcccgaa gttcgtccgg    360
gcccgtcaac tggtcgcgga caccgaggcg ttcgacggc cgcacctggt ccgggtcgtc    420
ttccgcaact cgggccccga ggccgcctgg ccgcgtcca aggacctcgc gggcggcgga    480
gccctcctgg acctgggctg tcacgcggtg gagctgtgcc ggtggctgct cgacggcgcc    540
gacgtcgagt cggtcagcgc ccgactgcag cgggtgcggc cgcccacga cgccgaagcg    600 gaccgcgcgt ccggcaccgc gggaaccgcg cgggtcgcgc tggaggacca ggcgctgctg    660
gtcatggagt tcgccgacgg cgcggtcggg cagtgcgacg tctcctgggt cacccagggc    720
ggtgagcagg tcaccgcgga gatcatcggc accaagggca gggtcgaggt cgacctgtgg    780
accggcatgg ggctgcgcgc ctactcggac aagggctatc aggacgtctg gatcccgag    840 cagggctggg tgcatccgga atgggagtgg atccgggcga gcggctacta ccaccaggac    900
ggcaccgtga tcgaggcggt gggccagggc atccccctca cccacggccc cgcggaagcg    960
ctcgcctcgg cccgtgtcct ggccaccggt taccgcagtc acgcggaggg cgggtactg   1020 cggctgtccg gcgcgccggt cggccctggc gcgtcgacga cggcggcggg ctcggaatga   1080

<210> SEQ ID NO 12
<211> LENGTH: 1260
<212> TYPE: DNA
<213> ORGANISM: Streptomyces kanamyceticus

<400> SEQUENCE: 12
atgagcaaga agctggcgct gttcggcgga actcccgtac ggaacgagga gttctacgac     60
ggcccgcaca tcgggccgca cgatctcgac cgcctcaaat ccgtcctcga ctcggggaac    120
ttcggcggca tccccttccc caacacccac acaccgcct tcgccgacct gttcaccggc    180
aagctcggcg ccccgtacgg cctgatggtc tccaacggca ccatcagtct ctccatcgcg    240
ctgcgcgccc tggcgtgcg tgccggggac gaggtgatca ccaccggcta cacctggatg    300
ggcacggccg cggcgatcgt gcacatcaac gccgtccccg tcctggtgga catcgacccc    360
acgacctggt gcatcgaccc ggcggcggtg gaggcggcga tcacccccgcg caccaaggtg    420
```

```
atcgtcccgg tccatctggg caatcagatc gccgacctcg acgcgctgcg ggcgatcgcc      480
gacaagcacg gactcgcgat cctggaggac accgcgcacg ggcacttcgc cgagtggcgg      540
gggcagtgcg tgggcaccca cggggacgcg ggcagcttca gcttcgagag cagcaagatc      600
atgactgccg gtgagggcgg cttcctggtg gccaggacg aggacgtgta ccagcggatg       660
atgtcgctgg ccaactgcgg ccgcaaggag ccgggttacg acggtttcgc gggccgcacc      720
ctgggctgga acgcccgcgc gagcgaactg caggccgcct tcatgatcgg gcaggtcgag      780
cagcacgacg cgctgcacgc caagcgggcg gcgagcgcgg cgaagctcac cgcggggctc      840
gccgagatcg gcggcttcac tcccgtgggg aacgacgacc cgaggatcac ccggcgccag      900
tactacgagg tcatctaccg cttcgacccc ccgcctggg aggggctgca ccgggacgag        960
gtcctctcgg cgatccttgc cgagggcatc gagctggagg gcgacgcctt ctacccgccc     1020
gtacacaaga gcgaactgtt cgcggtggac gccgtccact ggcccatgat cgccgagagg     1080
tacggcgatc ggatcggccc ggacagcgtc gacctgcccg tcgccgaccg cgccgccgcc     1140
gacgagtccg tgtgggtgca ccacgcgctg ctcaccggcg acgacaagga cctcggcgac     1200
atcctcgaag ccgtcgccaa ggtccgcgac aacctgcgag aactgcacga cgcgagctga     1260
```

<210> SEQ ID NO 13
<211> LENGTH: 1527
<212> TYPE: DNA
<213> ORGANISM: Streptomyces kanamyceticus

<400> SEQUENCE: 13

```
gtgcgcatca tctccgtaca ggaggcggcc acccgcacct tcgacgtctg cgtggtgggc       60
agcggcgcct ccggtgccat caccgccgcg gtgctcgccg aacggggcct gtccgtgctc      120
atcctcgaac agggcaccgc gatcccgccg ggcaccgacc acgacgacgt cgaggacccc      180
gacacctggg cgtacgcacg cgacggggaa ggctggagca aggagggcta tccctggagc      240
gccatggcgt tcggcggcgg cacggtgttc tacggcggca tctccttccg ctacgaacag      300
cgcgacctcg acccgccgcc cgcgctcctc ggcgacgccg actacgcgca ctggcggctg      360
cggctcgacg aactggagcc gcactacgac tgggtggagg accggctcgg cgtgagcggc      420
ccgtcccacg gccgggtggg cgactacgcc ttcccccact acgcgcgggg ctcgctgccg      480
cacaccccga tggcggcgc gctggcccgg ggcgccgacg ccctggggct gaccccgctg       540
tccaccccga tggcgatcag cggggccagg gaccggcacg gccccggctg cgccgagctg      600
acgccgtgca ccggcttcac ctgcccggtc aacgccaagg ccgatgtgat cagccgcatc      660
ctggcgcgcg ccgaggggga cgtgtccgtc gccctggaca ccagagcggt gcggttcgtg      720
gcctcggcac cggggcggc gaaacgtctc gaagtgctcg cggcagtcc ccgcagccgc        780 cgctcggtcc atgccgaccg cttcgtcctc gcggccaacg ccatccagtc cgccgcgctc      840
ctgctgcgtt cggcggaccg gcgcgagccg acggcatgg ggaactccag cggtcaggtg       900
ggccgccacc tggccatgaa gaacagcgtc tacgtccgcg gcaggaccca ggagcggatc      960
gtcgcccacc agccgctgcg ccatcgctac tccagcgtct gcgtcctgga ccacctgcgc     1020
ggtgcggagt tccccgggca gctgggcggg atcatctacg aggccaaccc gtgggaggac     1080
cccgaggccg accgtcctgg cgccggttcg ctgctccagc tggagtgcct cctcggcgac     1140
cgcccgcagg cccgcaacat ggtgcggctc gccaggagcc gggaccggga cgggctccag    1200
cgcatcgtca tggactaccg ccagcacccc ttggacggcg aacgcctgga cgtgctccag    1260
```

| | |
|---|---|
| gggaaggcga aggatgtact gcacgcggcc ggggccgagc gcaccgagtc cgtcgacagc | 1320 |
| gatttcgcga ccggcagcac gcatctgcac ggcacgctgc gcgccggtga cgaccccgcg | 1380 |
| acctcggtga ccgaccggac gggccggctg cacgactacg acaacgtgtg gtcggcggac | 1440 |
| ggcgcgacgt tccccttcgc cgggaacttc aatcccaccc tcaccatcca ggccaatgcc | 1500 |
| cggcggatcg cggtcggcat ctcctga | 1527 |

<210> SEQ ID NO 14
<211> LENGTH: 1179
<212> TYPE: DNA
<213> ORGANISM: Streptomyces kanamyceticus

<400> SEQUENCE: 14

| | |
|---|---|
| gtgtccacgc accccgtcct ggactggagc cgatccgccg aacacctgcg ccgctcccac | 60 |
| ggcgtcacca ccgaccccccg ccccgacgag gacggccact accccctgcgt actgacccgg | 120 |
| ggcagcggca ctcgcgtgta cgacctggac ggcaacgcct acctcgatct caccggatcc | 180 |
| ttcggctcgg tgctcatcgg gcacgcggaa ccggccgtcg tacgggcggt gaccgacgtc | 240 |
| ctgagcgaag gcaatctctt ctacaccggc gcgagcccgc gccgactggc cctcgcggag | 300 |
| cggctccttg actggttccc ctggtccgag caggccatct tctaccgcac ggggtcctgc | 360 |
| gcggtgtccg cggcggcccg gctcgcccag cacgcgaccg gccgcaaccg ggtgctgagt | 420 |
| tccggctacc acggctggca cgactggcac ctggaggcgg tgcccgaggc caagcccaag | 480 |
| accttcgagt cgtacgccac cgagttccac aacgacctgg cgctctaccg ctcctggctc | 540 |
| gaccggcacg cgcaggagat cgcggcggtc gtggtgacgc ccgagccgca ccgcttcgac | 600 |
| cacgcctact accaggagct gcgcgaggtg gccaaggagc acggctgcct gttcgtcgtg | 660 |
| gacgaggtca agaccggctt ccgggccggg gcgggcgggt tcagcgccct ggccgggatc | 720 |
| gagccggacg ccgtgaccgt ctccaagggc atggccaacg acacagcat ctccgccgtg | 780 |
| gtgggccagc gacagctcac ccaggagctg agcgaggcgc acgtctggtc cacctaccag | 840 |
| aacgaacagg tggggttcgc cgccgcgttg gcgtccctgg acttcctgga gcggcacgac | 900 |
| gtggcggccg tgacgcgccg cacgggtgag gcggtccggc agggcgtgct ccagctcttc | 960 |
| gccgaacacg gcctgcccgt cggggcgccg ggctggggac cgatgttcga gctggacttc | 1020 |
| gacgccgccg acgagggtct cgccgagcgg ctcgaagcgg cgctgctgcg ccacgggatc | 1080 |
| ttctgcgaca cgggcgacga cttcaacatg atgttccata ccgcggagca caccgacgag | 1140 |
| ctcctcgagc ggttcgccgc cgcgctcggc gacctctga | 1179 |

<210> SEQ ID NO 15
<211> LENGTH: 783
<212> TYPE: DNA
<213> ORGANISM: Streptomyces tenebrarius

<400> SEQUENCE: 15

| | |
|---|---|
| atggagcaac ggtacgtgct ggtcaccggg gccagtcgcg gtctgggacg gcgcagcgcc | 60 |
| gaggagctgg ccggccgagg gtggaccgtc gtcctggcct gccgcgacgt cgcggacgtc | 120 |
| gcgtcactgc tcgcgaccgt gcggcggccg ggcgccaggg cccacgcggt tccgatggac | 180 |
| gtgaccgacc cggacagcgt cgccgcgcg gtggacgccg tgcgcgaggt cggcgggcgg | 240 |
| ctgcacgccc tggtgaacaa cgccggggtg ttcgtcacg ccgaggagcg cttcccgggg | 300 |
| ctgacgccgg gggacgcgct cgacatcctg ctcaccaaca cctacggccc gctggtggtg | 360 |
| accagggcgt tcctccccct gttgcgcgcc gcgggcgggg cggcggtggt gaacgtgacc | 420 |

```
agccgcgacg ccgacgagga caccttcgac ggcgagttca cctgctaccg cgcgtccaag      480
gccgcgctga acgcgatgac caggaacctg cggtcgcgc tgcgccccga ccggatcgtc       540
gtcaacgcgg tcgatccggg gtggatcccc accgacatgg gcggtccgga ggccccggac     600
agcctggacg cggccgtgac ggcggtggtc gacgccgtcg agctggccgg gagcgaccgg     660
accggggtcc tgctcagggc tggccgcgac cccgcccctc cggtggcggc gccgagcgag     720
cccaaccagc ggcaccagcc ggacctcccg ccgcccccg tcccgcggtg gtcggcgtcg     780
tga                                                                    783

<210> SEQ ID NO 16
<211> LENGTH: 1383
<212> TYPE: DNA
<213> ORGANISM: Streptomyces tenebrarius

<400> SEQUENCE: 16
gtgaatgagg tgcgacgaat gcggctcggc acggtactgc tggtgagccc gaagacttcg       60
ttcgggcgtg atctgcaacg gacgtacgcg ggcgggctcg gcacggtctg caaggacgag      120
gacttcctgc tgccccccgct cgacctgatg cgcctggccg cgtcctgcg cgaggacgcc     180 gacgacatcg cgatcgccga cgaggaggtc accggcgtgg tcccctccgt ggagcccggc     240
accacggtga tctgccacgt ctcgctgccc agcctgctgg aggacgccga gcggctggcg     300
accttccgcg cgcagggcgc ccgctgctac gcctacacga gcatccgcag ccccgcccag     360
tggcggaccc tgttcgagcg gggcggctgc gagggcgtcc tgctccccga gtcgatctcc     420
ttcgcccgcg ccgcgctcgc cggcgaccac accgtgccgg gcctggtgac cccggactcg     480
ctgctcgacc cccggcacca ccagccggcc ttcggtgacc tggcggccga gccgctgccg     540
gccagggacc tggtcgacca cacgccgtac atgttccccc cgatcgcgcg caccgggatc     600
accagcatca acggcagctt cggctgcccc tacccgtgcc gcttctactg cccgtacccg     660
ctcagcgagg gccgcaagat ccgcacctac cccgtcgagc ggatcgtggc ggagttccgg     720
cagtgcgccg agctgggcat caccgcggcc gtcttccgcg acccggtgtt ctccttccac     780
cgcgaccgca ccctggagct gtgccaggcc ctcaaggccg ccgacaccgg ggtgccctgg     840
tggtgcgaga cccggatcga ccggctcgac gaggaggtcg tggccgcgct ggtcgacgcc     900
gggtgcgtcg gcgtcgaggt cggcgtggag agcggcgacc ccgacatgca ggcgaccgcc     960
gtccgcaagc gcctgaacct ggacaccgtc cggaagttcc acgcggtggc caggaaggcc    1020
gggctgaagc tggtcttcct gttcctgatc ggcctgccca gggagaccag gatgtcgatc    1080
cggcgcacct tcgacttcat cctggagctg gggctggccg acaccgagtt caacctcagc    1140
gtgatcaccc cctacccggg caccgagctg caccagatcc ggtggacaa ggggtggatc    1200 gacggctcgc agaacgcctt caccagccac aacgccgtga tgcacaccga cgagctgagc    1260
atcggcgacc tggagcgggc cagccggttc gtcgacgagc tgcacgcggt ctgcaaggcg    1320
gggcccgccg agcgggccga gttccaggcc agggtgcacg cctggtcgac cggtgacgcc    1380
tga                                                                  1383

<210> SEQ ID NO 17
<211> LENGTH: 1251
<212> TYPE: DNA
<213> ORGANISM: Streptomyces tenebrarius

<400> SEQUENCE: 17
```

| | |
|---|---:|
| gtgcgtgttc tccggctcac cccgttcttc caccacgact gcgtcacctc gtggccggcc | 60 |
| gagttcgacg cggtcggcgg gatgcagttg cagatcctgc ggctgtcccg cgagctggcc | 120 |
| cggcgcggcg tgcgccagca ggtgctcacg ctgggcttcc ccggcctgcc ccgggtgcgg | 180 |
| gtcgactcgc cgaacctggt cgtgcggatc accagggccc cgctgccccg gctgcggtcg | 240 |
| gagctgaccg gcctggtcgg gctcaaccag gcgtggctgg tcgccgcgct ggccgcgtgc | 300 |
| gtgcggctca ggcgcacctg gcgccccgac ctggtccacg tgcacgccga cggccagctc | 360 |
| tgggcgttgc tggcgggacc ggccgcgtcc cgcgtgctcg gcgtgcccta ctgcgtgacg | 420 |
| ctgcactgct cgcgcctgtc ggtgtaccag cccatgtcgt ggatcgacca gctccagcac | 480 |
| cggctggtcg tcgcggcgga gaagtgggcg ctgcgcgggg cctccggcgt gtcgaccctg | 540 |
| accgaccgca ccgcgtcggt ggtcgcctcc gcgctcgggg tgggcgcgga ggacgtcgac | 600 |
| gtggtccccg actcggtgga cacgtcgtcc actgtggaca gagcagaggg gcgcgtgctg | 660 |
| ctggagaagc tgggcgtgcc gtccgaccac gaggccgtcg gctacgtcgg ccgcgtcgcg | 720 |
| cacgagaagg gctggcccga cctcgtgcgc gtggccggcc cgctgtccga ccggaaggcg | 780 |
| accttcctgg tcgtcgggga cgggccgcag agcgggcgca tgcgcgacga ggtcgccgcc | 840 |
| gccggcctgt ccgaccggtt cctgttcacc gggttcctgc cccatcacga catcccggcg | 900 |
| gtcatggccg gtctggacgt gctcgtgatg ccgtcgcggc acgaggagct gggcgggagc | 960 |
| gcgctggagg cgatgctggc gggaacgccc gtggccgcct acgccgtggg tgggctgcgg | 1020 |
| gacaccgtgg gccacgtgac gccgtcgctg ctcgtgcctc ccggcgacgt cacggcgctc | 1080 |
| gcggaggccg ttcgtggtgt gctcgacgac ccgcggcccc accgcgacca ggtggccggc | 1140 |
| ggccgttcct ggctgaccga cctcttcgac ggcggtgccg ccgcgcgtcg ggtgatcgcc | 1200 |
| cactatgagc gtgtcctcag tggaaccgcc cgtctccgcc ctcaggaata g | 1251 |

<210> SEQ ID NO 18
<211> LENGTH: 1263
<212> TYPE: DNA
<213> ORGANISM: Streptomyces tenebrarius

<400> SEQUENCE: 18

| | |
|---|---:|
| gtgcggcggc ggggcggcgt gctggcgctc accccgttct tcctctaccc cgagtaccag | 60 |
| gactgctggt cggcccggtt cgactcgatg ggcgggatgc acctgctggt gcggcgctc | 120 |
| gtggaggaga tggccggcag gggcgtcccg caccgcgtgc tcaccatggc cccgcccggc | 180 |
| gtgcccaggg acctggccat cgcccgcaac gtcaccgtcc acgcgcgacg cctcccggtg | 240 |
| ttgccgatcc cgtcccagtt ggaggggtac ttcgggctgg tcggggcgtg ggccaagggg | 300 |
| agcctgctgt gggtcctgcg gaaccggagg cggctgcggc gggagatctc cctggtgcac | 360 |
| gcccactgcg acgggtcggg ctcggcgccg ttctacggct ggctcatcgc gcgggcgctg | 420 |
| ggcgtgccgc tggtggcgca gatccactcc agccggttcc tgagccagca ccccacgacg | 480 |
| ttgtgggaac gggtcaccga cccggccgcg aagtgggcgc agcggttcac cgtccgcaac | 540 |
| gcggcggcgg tgctgatgct caccgagaag gcccgcaccg agatgcggga cgcggcggcg | 600 |
| ctggaccccc ggcgcgtcca ccggctgccc tacctggcca cgaccgcctt cgccgagggc | 660 |
| gacaccgagg agcggaggac cgagatcagg cggcgcttcg gcctggacac cggccagccc | 720 |
| gtcgtcctct acgtcgggcg gatcgcggcc gagaagggcg tggagttctt cgtcgaggcc | 780 |
| gccgccgaac tgcggcggcg cgggcgtaac tgccggttcc tcgtcgcggg ggacggcccg | 840 |
| acccgccagg agatcgagaa gctggccgag gacaggggcg tcgccgaccg gatcacgatc | 900 |

```
accggtttcc tgccgcacga gctgatcccc tcggtgatgg cattgtccca gctcgtggtc    960
ctgccctccc ggtacgagga actgggcatc gtgatcctgg agtgcatgag catgcgccgg   1020
ccgatcgtcg cgcacgacgt caacggcgtg cacaagctca tcgagcatgg caggaccggg   1080
ctgttggtgc cgccgttcga cacgcccgcg atggccgacg ccatcgaggc gctgctggac   1140
gacccggagc tgcgggagcg gatcgccgag accgccgccc gctgccgtc cgcgaagtac    1200 tcgctgacca cggcggcgga ccagctcacg gacatctacc gggagctggg cgtatgcgtc   1260
tga                                                                 1263
```

<210> SEQ ID NO 19
<211> LENGTH: 471
<212> TYPE: DNA
<213> ORGANISM: Bacillus circulans

<400> SEQUENCE: 19

```
atgattagct ggacgaaagc ttttaccaag ccgttaaagg ggagaatttt catgcccaac     60
ttatttgtct acgggactct gcgtgaggga gaaaacaacc acaagtatat gaagaagcc    120 accctgcttt cgcgaaaggc cagcatagcc ggttccttgg tagataccgg caacggttac    180
cccggcttac tgctggaaaa tcagctggtg gcgggcgagt ggtatgaagt ctcggaagaa    240
acgctgaaac ggatagatga gctggaagag tatttcggtc ccggggatac aagaaactta    300
tttgacagaa tcgaatgcca agtaaacgag agcggcggaa cacatctggg ttggacgtac    360
gtgtacaacc gggacgatta cctggaaaca aggttttccg actggaaaca ataccggctg    420
cagcatgctt ccggaataga ggagaagcaa gatgtgcctc actcgttatg a            471
```

<210> SEQ ID NO 20
<211> LENGTH: 909
<212> TYPE: DNA
<213> ORGANISM: Bacillus circulans

<400> SEQUENCE: 20

```
atgtgcctca ctcgttatga cgagaaattt tcgattgca gaaaatcgca gataatcgct      60
tatttggact cacaacaggt ccccgtcatt cctctatttt ataacagtta tcaaagcaca    120
gcggaaattt accgccagat ctttatcgaa aataagagca aatggaagta ttcagagcct    180 tcttttccg acgatgattt actaagaaaa ggaattaggc tgttcgggc ttcttttccc     240 gacttcagcc aggcttcgga ttgtttaaag gatctgctgg cccggcataa actcgttttc    300 gtatggggg acgagtattg tctgccttac cggaaggaag ccttccaggc cattcattcc    360
actcattcgc ttgttgtcac gggctatgac ggtgagaaca aggcatacta cgtggaagat    420 tgggacggc tctacggata tttgccggct gtacatttgg aagcggcttt cgacagtctg    480
tccaggcaga tgaggacatt gttggttctg gaactgaacg acgaggaaat gcgggaaaac    540
aaacaagagg atacagattt gttccggaag tggctgcaag ccttcgagga cgactatatc    600
ttctacgacc gggtgctgct ggatatgcgc gattatgagg aaaaccggct gatctcgatg    660
gatcacggac ttcgtttaat cgccgcatcc cggcatgttt tctccaagtt tcttcattat    720
atagatgacg ccccggagga ggtcggcctc cttatccgca accatcaact cgctaaccat    780
atcgcggcca tcgtcaggcg gtacattatc gccaaacaga ttgattggga cggggcagct    840
tgcaagattc ggcaattaag agagcaagag gatgactta tgcggaagct aaagagccgt    900
tacggctaa                                                            909
```

<210> SEQ ID NO 21
<211> LENGTH: 264
<212> TYPE: DNA
<213> ORGANISM: Bacillus circulans

<400> SEQUENCE: 21

| | | | | | |
|---|---|---|---|---|---|
| atgtctttag | aaactcagga | aaatgttcgg | accgctcaaa | ttgtatcttg | cgtgaatgaa | 60 |
| attctgcaga | cgaaggaatt | cattaccccg | gaaaccgatt | tgtttctgct | tggcttggac | 120 |
| tcggtaaccg | ccgttaatct | gatcgtcagt | ttggaaagcc | atttcgggat | cacgtttaac | 180 |
| gacgacgaac | tgatcgtgga | aaattttttcg | acggtgcgga | aaattacgga | acatgtgacg | 240 |
| gtcaaacttg | aggaagccct | atga | | | | 264 |

<210> SEQ ID NO 22
<211> LENGTH: 1259
<212> TYPE: DNA
<213> ORGANISM: Bacillus circulans

<400> SEQUENCE: 22

| | | | | | |
|---|---|---|---|---|---|
| atgaagttca | ctcatccgct | ggattattat | cgtctgaacg | gcaaacaaat | cctgtggtac | 60 |
| atgaatatcg | gcgaagatca | ggacagccag | gcgtcgaatt | actttccctc | cgtcaaggac | 120 |
| cctcaatccg | agaagattgt | cgtgcagcag | gagcaacagc | ttctcttttct | ggcgaggccg | 180 |
| caggacacgt | tattttttca | tacgatgccg | gagcaagcct | ttctcgatta | ttggaaagag | 240 |
| cgccgcctct | ccttgccgtc | gataatttgt | tgcgacaaac | tttcgcaagt | gcctgatctt | 300 |
| gagcgttata | cgattatccc | gtttattgtt | tcggatcaac | tgcttgagct | gaagcggcgg | 360 |
| tatccgcata | tggatatcat | tgcgccggat | ttggcggtct | gccgggaaat | caatcataag | 420 |
| ttcaatacga | aagacttat | ggagaggaac | gggtttaacg | tcacaacggg | ttatttctgc | 480 |
| agcgatatcg | agagcttgga | gcatgcctac | gaacagctca | tttccgccgg | cttttccaaa | 540 |
| tgcgtgttga | aagttccata | cggctcgtcg | ggtaaaggtc | tcaaagtcat | cgacaacgaa | 600 |
| cggaatttcc | gttttttgct | gaattatatt | caaaaccgcc | agacaaacgt | cgacctgctc | 660 |
| ctggaaggct | ggcatcccca | ccgtctcagc | ctgacgtctc | agcttttcat | taccgaatat | 720 |
| gaagtccatc | ttctggccgt | caccgagcaa | atcatagacc | cgaacggtgt | ctataaagga | 780 |
| acgaatttta | cgcctgcctt | atcgcaatcg | gaagcggccg | attatcgtga | agaaatctta | 840 |
| cgggcaggag | aactgatacg | gcagatgggg | tataggggcg | tgcttgggat | cgattcgatc | 900 |
| ctcgatacga | acggagaact | gattccggtt | atcgagatta | cgccaggct | cactcaggtc | 960 |
| acctatattc | ttccgttggt | tatcgaacag | aaaaagcgtt | atgagtttgt | cgaaagcagg | 1020 |
| gtgctggtgt | ttaattccag | agcggatctg | gattttgaag | attacgaaaa | cgatctctcg | 1080 |
| gaagtgaccc | gcgatttacc | ggtccgaatc | gatctttaca | atttctgcaa | ggcttcggga | 1140 |
| gcctttaaaa | acacctataa | gctctttgtg | ttagtttctg | cccacaattc | gaacagctg | 1200 |
| ataaaagccc | gaagcctgct | tgacgagctg | aacacgaaaa | tgacaacggc | tgttcatta | 1259 |

<210> SEQ ID NO 23
<211> LENGTH: 1287
<212> TYPE: DNA
<213> ORGANISM: Bacillus circulans

<400> SEQUENCE: 23

| | | | | | |
|---|---|---|---|---|---|
| atgaacctgg | atcaagctga | aatcacggcc | ttaacgaaaa | ggtttgagac | tccttttttat | 60 |
| ttgtatgacg | gcgatttttat | cgaagcgcat | taccggcaat | taagaagccg | gacgaacccg | 120 |

```
gcgatccagt tttatttgtc cctaaaagca aataacaata ttcatctggc caaattgttc      180
cggcagtggg gacttggcgt cgaggttgca tccgccggag aactcgcttt agcccggcat      240
gccggatttt cagccgaaaa catcattttc tcggaccggg gaagaagcg gagcgagctc       300 gagattgccg ttcaaagcgg gatttactgc atcatcgcgg aatccgttga agaactcttt      360
tacatagaag aactggctga aaagaaaaac aaaacggccc gcgtcgcgat ccggatcaat      420
cccgataaaa gcttcggcag cacggccatc aaaatgggcg gagtaccgag acagttcgga      480
atggacgaat ccatgctgga tgccgtaatg gatgccgtcc gctctcttca attcaccaaa      540
tttatcggga tacacgtata taccggaacc cagaatctga ataccgacag cattatcgag      600
tcgatgaaat acaccgtaga tctaggcaga acatttatg aacgatacgg aatcgtctgt       660
gaatgtatta tcttggcgg agggttcgga gtcccgtatt tttcacacga aaaggcactg      720
gatatcggca aaatcacgcg tacggtcagc gattacgttc aagaggcgag ggatacacgg      780
ttcccgcaaa cgacctttat tatcgaaagc ggaagatact tattggctca gcggccgtg       840 tatgtaaccg aggtgcttta ccggaaagcg tccaaggag aagttttgt gatcgtagac        900 gggggaatgc accaccatgc ggcctccact ttccggggaa gaagtatgcg gagcaactac      960
cccatggaat atattcccgt tagggaagac tccggccgtc gcgaactcga aaaagtcacc     1020
attgccggtc ctctctgtac gcccgaagat tgtctaggga aggatgtcca tgtgccggcc     1080
ttgtatccgg gcgacctcgt atgtgtgttg aactcgggag cttacggact gagctttagc     1140
ccggttcatt ttctgggca cccgacgccc attgaaattc tcaaacgaa cggttcatac       1200 gagctgatca gacggaaagg aacggcggat gatatagtcg ccacccagct gcagacagaa     1260
tcaaatctcc tctttgtgga caaatag                                         1287

<210> SEQ ID NO 24
<211> LENGTH: 1026
<212> TYPE: DNA
<213> ORGANISM: Bacillus circulans

<400> SEQUENCE: 24
atgattgcat tggatacgat tcagtattat ggccaaattc caggcgtcaa ccattataac       60
ggcaagaaag aatttatgga aaacgccgtt aaaatcgcgc agctgtccga tgcttacggc      120
atagtcgggt ccctgtcgtt ttttaaccat tccgtattgg acccttgggc cgtaagctcg      180
gttattatgc ggcatacgga acgtcatgtt cctctaattg cgcttcagcc ctacatgtat      240
cctccctata cggctgccaa gttaattcag agcttcactt atttgtacga ccggcggatc      300
gacttgaata tgatcaccgg ggccgttacc ggcgagctcc agcaaaccgg gggctatatc      360
gatcattcgt ccgctacaa gaaacttcac gaatatgttc aggtgctccg tctgctgctt       420
gaatccgatt ctgccgtttc gttcaaaggg gactattatg agctgaataa tttggagttc      480
aagcctttgc tgccgacaa acggcttttc ccgcgcatat ttatgtccgg ttcttccgag       540
gaagggcttg aaacgggttt gaaagcggcg gatttcgtcg ttactcatcc gggaccgctg      600
gaacatttta acgccatttt agcgaaaaag gtgcagggat cggctgttca aagtgccata      660
agaatcgaga ttatcgccag agaatcgcg gagcaagcat ggaagatcgc tcatgcccgt       720
tatcccggca accggcaggg gaagatccag ctccggatga aacaaattc ggaatcaagc       780 tggcagcgga tgctggccga actggcttta gcgagtgaaa cgtacgatga agtcttctgg      840
atgggcgggt acatgaacgg cggaatttac agtcccgtgt tagtcgggga ttacgagcaa      900
```

-continued

```
gtggccgctt atttgaatga gtattacaaa ctcggcgtga aagccgtgtt gctgggttcc      960
atgtacagcg aggaggattt tattcatttc agccgggtga aggaaggaat ttcgaatccg     1020
gtctag                                                                 1026
```

<210> SEQ ID NO 25
<211> LENGTH: 576
<212> TYPE: DNA
<213> ORGANISM: Bacillus circulans

<400> SEQUENCE: 25

```
gtggctcatc cgaatttgca gcagtcccgt gtcaacaaac gttgggtgga ggaattgaaa       60
aaacatcccg gcgaggttac cgtgcatgaa ctgtacggcg cgtatccgga gaaggtattg      120
gatatcgggc gggagcaggc tttgctggcg gaatgtgaac gtctcgtgct gcagtttccg      180
cttcaatggt acagcacacc gccgcttctg aagcagtggc tcgatgaagt gttcacaacg      240
gggtggctgt tcggtccggg cggtaaagcc gtagccggaa agaactcct gatcgccgtt       300 tctatcgggg gagcggcgga gacttacgag gcgggcggcc tgatcgggta cacgatcagt      360
gaattgaccc gccctctgca agctttcgcc aatcagatcg gcatgacgat gcttccgcac      420
tttaaatttc acggtgcgaa tcaggcgcg gacgaactga tcgagagcag cgcggagcga       480
tacgtcaggc atatcttgac tcccgagctt gatccccgga ttgcccggcg gagaatgctt      540
aatgacatga aacagaagat gcaggcctcc ctgtaa                                576
```

<210> SEQ ID NO 26
<211> LENGTH: 1266
<212> TYPE: DNA
<213> ORGANISM: Streptomyces fradiae

<400> SEQUENCE: 26

```
gtgcgtgtgc tgcggctcac ccccttcttc caccacgact gcgtcaccgc ctggcccgcg       60
gagttcgacg ccgtcggggg catgcaggtg cagatcctcc gcctctcgcg ggaactggcc      120
gaccgcggcg tggagcagct cgtcatgacc gtcgggttcc ccggcctgcc cagggagcgc      180
gtcgaccggc ccggcctccg ggtccgggtc accggggcgc cgctgccccg gctgcgctcc      240
gaactgaccg gcctcgtggg gctcaaccag gcgtggctcg ccgcggtgct gacggcctgt      300
gcgccgctgc gccgcacctg gagggcccgac ctggtgcacg tccacgcgga cggccagctc      360
tgggcgctgc tcgccgggcc gctcgtctcg cgtctggtcg gcgcgccgta ctgcctcacc      420
ctgcactgct cgcggctggc ctcgtacgag ccgatgtccc gcttcgaccg gctccagcac      480
cggctggtgg cggcggccga gcggtacgcg ctgcggcggg cgcgccgggt gtcgacgctg      540
acctcgcgca ccgcggacac ggtggcgcgc tgctgccgc tcgaccgggc cctggtggac      600
gtgctgcccg actcggtcgg cgacgtgcgg ccggtggcgc ggccggaggc cgaggagtac      660
gtgcggtcgc tcggcgtgcc cgccggggcg gcggtggtgg gctgggtcgg ccgggtcgcg      720
cacgagaagg ggtggcggga cttcgtcgcg atggcggagc ggtgggacgc cggtcgggc       780 gccccggggg cggtgttcgc cgtggtgggc gacgggccgc agcgggagcg gatgcgggag      840
gcggtcgagg cggcggggct cgcggaccgg ttcgtgttca ccggtttcct gccccatgac      900
gccgtgccgt ccgtgatgac ggcgctggac gtcctcgtca tgccgtccgc ccacgaggag      960
ctggccggca gcgcgctgga ggccatggtg tgcggcacgc ccgtcgcggg ctacgcggtc     1020
ggcgggctgc gcgacacggt cggctcggtc acgccctccc tgctcgtccc gcggggcgac     1080
gtggcggcgc tgacccgcgc cgccggcgac gcggtcacgg acgccgaacg gcaccgcaag     1140
```

```
acggtcgcgg cggccgttcc cgacctgctg ggccggtacg gcgcggacac cgtcgagcgg    1200
gcgctggagc actaccggct ggccgtcggc cgggcgtccg agggggtgc cgggtgggcg     1260 ccgtga                                                                1266

<210> SEQ ID NO 27
<211> LENGTH: 27
<212> TYPE: DNA
<213> ORGANISM: Artificial Sequence
<220> FEATURE:
<223> OTHER INFORMATION: forward primer for kanA-kanB

<400> SEQUENCE: 27
cccggatccg aatccccctt cgtgacg                                          27

<210> SEQ ID NO 28
<211> LENGTH: 30
<212> TYPE: DNA
<213> ORGANISM: Artificial Sequence
<220> FEATURE:
<223> OTHER INFORMATION: reverse primer for kanA-kanB

<400> SEQUENCE: 28
gtgactagtg ttcgtcgacc accgcgtcga                                       30

<210> SEQ ID NO 29
<211> LENGTH: 28
<212> TYPE: DNA
<213> ORGANISM: Artificial Sequence
<220> FEATURE:
<223> OTHER INFORMATION: forward primer for kanK

<400> SEQUENCE: 29
gcttctagaa ctccggagca cccgtgca                                         28

<210> SEQ ID NO 30
<211> LENGTH: 30
<212> TYPE: DNA
<213> ORGANISM: Artificial Sequence
<220> FEATURE:
<223> OTHER INFORMATION: reverse primer for kanK

<400> SEQUENCE: 30
gtgaagcttc gtggtgccgg acaggccta                                        30

<210> SEQ ID NO 31
<211> LENGTH: 30
<212> TYPE: DNA
<213> ORGANISM: Artificial Sequence
<220> FEATURE:
<223> OTHER INFORMATION: forward primer for kanC

<400> SEQUENCE: 31
gggacctcta gaacgcggtg gtcgacgaac                                       30

<210> SEQ ID NO 32
<211> LENGTH: 36
<212> TYPE: DNA
<213> ORGANISM: Artificial Sequence
<220> FEATURE:
<223> OTHER INFORMATION: reverse primer for kanC

<400> SEQUENCE: 32
tcttccaagc ttactagttg tcggcggtcg ccccga                                36
```

<210> SEQ ID NO 33
<211> LENGTH: 30
<212> TYPE: DNA
<213> ORGANISM: Artificial Sequence
<220> FEATURE:
<223> OTHER INFORMATION: forward primer for kanD

<400> SEQUENCE: 33
gaccgctcta gacacctccg aggtcctctc                                30

<210> SEQ ID NO 34
<211> LENGTH: 34
<212> TYPE: DNA
<213> ORGANISM: Artificial Sequence
<220> FEATURE:
<223> OTHER INFORMATION: reverse primer for kanD

<400> SEQUENCE: 34
tgaaaagctt actagtgggt gacgagacgc cggg                           34

<210> SEQ ID NO 35
<211> LENGTH: 33
<212> TYPE: DNA
<213> ORGANISM: Artificial Sequence
<220> FEATURE:
<223> OTHER INFORMATION: forward primer for kanE

<400> SEQUENCE: 35
acatctagag gctccggaag accgccgacg cca                            33

<210> SEQ ID NO 36
<211> LENGTH: 33
<212> TYPE: DNA
<213> ORGANISM: Artificial Sequence
<220> FEATURE:
<223> OTHER INFORMATION: reverse primer for kanE

<400> SEQUENCE: 36
tcgaagctta ctagtgagac gaggaggacc ctt                            33

<210> SEQ ID NO 37
<211> LENGTH: 30
<212> TYPE: DNA
<213> ORGANISM: Artificial Sequence
<220> FEATURE:
<223> OTHER INFORMATION: forward primer for kanF

<400> SEQUENCE: 37
cgaggctcta gagccggacc agaacccatt                                30

<210> SEQ ID NO 38
<211> LENGTH: 36
<212> TYPE: DNA
<213> ORGANISM: Artificial Sequence
<220> FEATURE:
<223> OTHER INFORMATION: reverse primer for kanF

<400> SEQUENCE: 38
tagaacaagc ttactagtac gtcgggtgtc gtacgg                         36

<210> SEQ ID NO 39
<211> LENGTH: 30
<212> TYPE: DNA
<213> ORGANISM: Artificial Sequence
<220> FEATURE:
<223> OTHER INFORMATION: forward primer for kanI-kacL

<400> SEQUENCE: 39
gatcgctcta gacacctggt tctggttccc                                   30

<210> SEQ ID NO 40
<211> LENGTH: 36
<212> TYPE: DNA
<213> ORGANISM: Artificial Sequence
<220> FEATURE:
<223> OTHER INFORMATION: reverse primer for kanI-kacL

<400> SEQUENCE: 40
aggggaaagc ttactagtgt caggagatgc cgaccg                            36

<210> SEQ ID NO 41
<211> LENGTH: 30
<212> TYPE: DNA
<213> ORGANISM: Artificial Sequence
<220> FEATURE:
<223> OTHER INFORMATION: forward primer for kacA

<400> SEQUENCE: 41
ggcgtctaga taccgggaga tcgggctgtg                                   30

<210> SEQ ID NO 42
<211> LENGTH: 35
<212> TYPE: DNA
<213> ORGANISM: Artificial Sequence
<220> FEATURE:
<223> OTHER INFORMATION: reverse primer for kacA

<400> SEQUENCE: 42
acaaagctta ctagttgctc atagcgactc cttgt                             35

<210> SEQ ID NO 43
<211> LENGTH: 29
<212> TYPE: DNA
<213> ORGANISM: Artificial Sequence
<220> FEATURE:
<223> OTHER INFORMATION: forward primer for nemD

<400> SEQUENCE: 43
cactctagac atcgccgtcc tctccccgt                                    29

<210> SEQ ID NO 44
<211> LENGTH: 33
<212> TYPE: DNA
<213> ORGANISM: Artificial Sequence
<220> FEATURE:
<223> OTHER INFORMATION: reverse primer for nemD

<400> SEQUENCE: 44
tcaaagctta ctagtggcgc agatacggcg cac                               33

<210> SEQ ID NO 45
<211> LENGTH: 27
<212> TYPE: DNA
<213> ORGANISM: Artificial Sequence
<220> FEATURE:
<223> OTHER INFORMATION: forward primer for tobM1

<400> SEQUENCE: 45
ccgtctagac cgcccttttcc ccgcaac                                     27

<210> SEQ ID NO 46

<211> LENGTH: 33
<212> TYPE: DNA
<213> ORGANISM: Artificial Sequence
<220> FEATURE:
<223> OTHER INFORMATION: reverse primer for tobM1

<400> SEQUENCE: 46
gataagctta ctagtcacac cgtcctattc ctg                                    33

<210> SEQ ID NO 47
<211> LENGTH: 26
<212> TYPE: DNA
<213> ORGANISM: Artificial Sequence
<220> FEATURE:
<223> OTHER INFORMATION: forward primer for tobM2

<400> SEQUENCE: 47
cgatctagac cgggaggcga ccgtgt                                            26

<210> SEQ ID NO 48
<211> LENGTH: 33
<212> TYPE: DNA
<213> ORGANISM: Artificial Sequence
<220> FEATURE:
<223> OTHER INFORMATION: reverse primer for tobM2

<400> SEQUENCE: 48
gcgaagctta ctagttcaga cgcatacgcc cag                                    33

<210> SEQ ID NO 49
<211> LENGTH: 31
<212> TYPE: DNA
<213> ORGANISM: Artificial Sequence
<220> FEATURE:
<223> OTHER INFORMATION: forward primer for gtmG

<400> SEQUENCE: 49
tgtcctctag agctgcccgg tcacttcccg c                                      31

<210> SEQ ID NO 50
<211> LENGTH: 33
<212> TYPE: DNA
<213> ORGANISM: Artificial Sequence
<220> FEATURE:
<223> OTHER INFORMATION: reverse primer for gtmG

<400> SEQUENCE: 50
aaaaagctta ctagtcactc ttccggaaga atc                                    33

<210> SEQ ID NO 51
<211> LENGTH: 27
<212> TYPE: DNA
<213> ORGANISM: Artificial Sequence
<220> FEATURE:
<223> OTHER INFORMATION: forward primer for btrG-btrH

<400> SEQUENCE: 51
ttctctagat ctaggaaacc gcatgcc                                           27

<210> SEQ ID NO 52
<211> LENGTH: 35
<212> TYPE: DNA
<213> ORGANISM: Artificial Sequence
<220> FEATURE:
<223> OTHER INFORMATION: reverse primer for btrG-btrH

<400> SEQUENCE: 52

-continued ggctacgtaa aactagtggt ttatccgctt ttgct        35

<210> SEQ ID NO 53
<211> LENGTH: 27
<212> TYPE: DNA
<213> ORGANISM: Artificial Sequence
<220> FEATURE:
<223> OTHER INFORMATION: forward primer for btrI-btrJ

<400> SEQUENCE: 53
acctctagac ggaaaccgcc atcccat        27

<210> SEQ ID NO 54
<211> LENGTH: 35
<212> TYPE: DNA
<213> ORGANISM: Artificial Sequence
<220> FEATURE:
<223> OTHER INFORMATION: reverse primer for btrI-btrJ

<400> SEQUENCE: 54
tcctacgtaa aactagtgag ttaatgaaca gccgt        35

<210> SEQ ID NO 55
<211> LENGTH: 27
<212> TYPE: DNA
<213> ORGANISM: Artificial Sequence
<220> FEATURE:
<223> OTHER INFORMATION: forward primer for btrK-btrO

<400> SEQUENCE: 55
agctctagaa agcccgaagc ctgcttg        27

<210> SEQ ID NO 56
<211> LENGTH: 35
<212> TYPE: DNA
<213> ORGANISM: Artificial Sequence
<220> FEATURE:
<223> OTHER INFORMATION: reverse primer for btrK-btrO

<400> SEQUENCE: 56
gtttacgtaa aactagttcc ctagaccgga ttcga        35

<210> SEQ ID NO 57
<211> LENGTH: 27
<212> TYPE: DNA
<213> ORGANISM: Artificial Sequence
<220> FEATURE:
<223> OTHER INFORMATION: forward primer for btrV

<400> SEQUENCE: 57
tattctagaa ttgacttata actcaat        27

<210> SEQ ID NO 58
<211> LENGTH: 35
<212> TYPE: DNA
<213> ORGANISM: Artificial Sequence
<220> FEATURE:
<223> OTHER INFORMATION: reverse primer for btrV

<400> SEQUENCE: 58
cattacgtaa aactagtatc cgaacgtcac ataag        35

<210> SEQ ID NO 59
<211> LENGTH: 27
<212> TYPE: DNA

```
<213> ORGANISM: Artificial Sequence
<220> FEATURE:
<223> OTHER INFORMATION: forward primer for aprD3

<400> SEQUENCE: 59
ggttctagat gatggacgtg gccgcga                                       27

<210> SEQ ID NO 60
<211> LENGTH: 33
<212> TYPE: DNA
<213> ORGANISM: Artificial Sequence
<220> FEATURE:
<223> OTHER INFORMATION: reverse primer for aprD3

<400> SEQUENCE: 60
cttaagctta ctagtgggcc gtcggtcgtc ctg                                33

<210> SEQ ID NO 61
<211> LENGTH: 30
<212> TYPE: DNA
<213> ORGANISM: Artificial Sequence
<220> FEATURE:
<223> OTHER INFORMATION: forward primer for aprD4

<400> SEQUENCE: 61
ggctctagaa accccaccct caccatccag                                    30

<210> SEQ ID NO 62
<211> LENGTH: 33
<212> TYPE: DNA
<213> ORGANISM: Artificial Sequence
<220> FEATURE:
<223> OTHER INFORMATION: reverse primer for aprD4

<400> SEQUENCE: 62
cgcaagctta ctagtatcgt gtggtctccg gct                                33
```